United States Patent
Chackerian et al.

(10) Patent No.: US 12,162,916 B2
(45) Date of Patent: Dec. 10, 2024

(54) COMPOSITIONS TARGETING APOPTOSIS-ASSOCIATED SPECK-LIKE PROTEIN WITH CASPASE ACTIVATION AND RECRUITMENT DOMAIN (ASC) AND METHODS OF USE

(71) Applicant: UNM Rainforest Innovations, Albuquerque, NM (US)

(72) Inventors: Bryce Chackerian, Albuquerque, NM (US); Kiran Bhaskar, Albuquerque, NM (US); Jonathan P. Hulse, Albuquerque, NM (US)

(73) Assignees: UNM Rainforest Innovations, Albuquerque, NM (US); Bryce Chackerian, Albuquerque, NM (US); Kiran Bhaskar, Albuquerque, NM (US); Jonathan Hulse, Albuquerque, NM (US)

( * ) Notice: Subject to any disclaimer, the term of this patent is extended or adjusted under 35 U.S.C. 154(b) by 0 days.

(21) Appl. No.: 18/637,070

(22) Filed: Apr. 16, 2024

(65) Prior Publication Data
US 2024/0279295 A1 Aug. 22, 2024

Related U.S. Application Data

(63) Continuation of application No. PCT/US2023/031605, filed on Aug. 31, 2023.

(60) Provisional application No. 63/402,601, filed on Aug. 31, 2022.

(51) Int. Cl.
*C07K 14/47* (2006.01)
*A61K 39/00* (2006.01)

(52) U.S. Cl.
CPC .... *C07K 14/4747* (2013.01); *A61K 39/00115* (2018.08); *A61K 2039/5258* (2013.01); *C12N 2795/18123* (2013.01); *C12N 2795/18134* (2013.01)

(58) Field of Classification Search
None
See application file for complete search history.

(56) References Cited

U.S. PATENT DOCUMENTS

| | | |
|---|---|---|
| 4,722,840 A | 2/1988 | Valenzuela et al. |
| 5,234,809 A | 8/1993 | Boom et al. |
| 6,482,933 B1 | 11/2002 | Bertin |
| 7,776,616 B2 | 8/2010 | Heath et al. |
| 7,957,913 B2 | 6/2011 | Chinitz et al. |
| 9,012,208 B2 | 4/2015 | Selden et al. |

FOREIGN PATENT DOCUMENTS

| | | |
|---|---|---|
| EP | 0421635 B1 | 7/1995 |
| WO | 0032227 A2 | 6/2000 |
| WO | 02056905 A2 | 7/2002 |
| WO | 03024481 A2 | 3/2003 |
| WO | 03092714 A2 | 11/2003 |
| WO | 2004007538 A2 | 1/2004 |
| WO | 2014164703 A1 | 10/2014 |
| WO | 2022148954 A1 | 7/2022 |
| WO | 2024049946 A1 | 3/2024 |

OTHER PUBLICATIONS

Crossey et al. (2015) "A Cholesterol-Lowering VLP Vaccine that Targets PCSK9", Vaccine, 33(43):1-9.
Jiang et al. (Sep. 21, 2021) "Proteopathic tau Primes and Activates Interleukin-1β via Myeloid-Cell-Specific MyD88-and NLRP3-ASC-Inflammasome Pathway", 36(12):109720 (12 pages).
Kozlovska et al. (1996) "RNA Phage Q beta Coat Protein as a Carrier for Foreign Epitopes", Intervirology, 39(1-2):9-15.
Silva et al. (2013) "Apoptosis-Associated Speck-like Protein Containing a Caspase Recruitment Domain Inflammasomes Mediate IL-1β Response and Host Resistance to Trypanosoma Cruzi Infection", The Journal of Immunology, 191(6):3373-3383.

*Primary Examiner* — Nicole Kinsey White
(74) *Attorney, Agent, or Firm* — MUETING RAASCH GROUP

(57) ABSTRACT

An immunogen includes an immunogenic carrier and an antigenic apoptosis-associated speck-like protein containing a caspase activation and recruitment domain (ASC) peptide linked to the immunogenic carrier. In one or more embodiments, the immunogenic carrier is a Qβ virus-like particle (VLP). The immunogen may be formulated into a composition useful for treating inflammatory medical conditions.

22 Claims, 17 Drawing Sheets

Specification includes a Sequence Listing.

SEQUENCE LISTING

```
Sequence total quantity: 23
SEQ ID NO: 1                moltype = AA   length = 195
FEATURE                     Location/Qualifiers
source                      1..195
                            mol_type = protein
                            organism = synthetic construct
SEQUENCE: 1
MGRARDAILD ALENLTAEEL KKFKLKLLSV PLREGYGRIP RGALLSMDAL DLTDKLVSFY    60
LETYGAELTA NVLRDMGLQE MAGQLQAATH QGSGAAPAGI QAPPQSAAKP GLHFIDQHRA   120
ALIARVTNVE WLLDALYGKV LTDEQYQAVR AEPTNPSKMR KLFSFTPAWN WTCKDLLLQA   180
LRESQSYLVE DLERS                                                   195

SEQ ID NO: 2                moltype = AA   length = 193
FEATURE                     Location/Qualifiers
source                      1..193
                            mol_type = protein
                            organism = synthetic construct
SEQUENCE: 2
MGRARDAILD ALENLSGDEL KKFKMKLLTV QLREGYGRIP RGALLQMDAI DLTDKLVSYY    60
LESYGLELTM TVLRDMGLQE LAEQLQTTKE ESGAVAAAAS VPAQSTARTG HFVDQHRQAL   120
IARVTEVDGV LDALHGSVLT EGQYQAVRAE TTSQDKMRKL FSFVPSWNLT CKDSLLQALK   180
EIHPYLVMDL EQS                                                     193

SEQ ID NO: 3                moltype = AA   length = 15
FEATURE                     Location/Qualifiers
source                      1..15
                            mol_type = protein
                            organism = synthetic construct
SEQUENCE: 3
GSGAAPAGIQ APPQS                                                    15

SEQ ID NO: 4                moltype = AA   length = 19
FEATURE                     Location/Qualifiers
source                      1..19
                            mol_type = protein
                            organism = synthetic construct
SEQUENCE: 4
NPSKMRKLFS FTPAWNWTC                                                19

SEQ ID NO: 5                moltype = AA   length = 23
FEATURE                     Location/Qualifiers
source                      1..23
                            mol_type = protein
                            organism = synthetic construct
SEQUENCE: 5
CKDLLLQALR ESQSYLVEDL ERS                                           23

SEQ ID NO: 6                moltype = AA   length = 15
FEATURE                     Location/Qualifiers
source                      1..15
                            mol_type = protein
                            organism = synthetic construct
SEQUENCE: 6
MGRARDAILD ALENL                                                    15

SEQ ID NO: 7                moltype = AA   length = 12
FEATURE                     Location/Qualifiers
source                      1..12
                            mol_type = protein
                            organism = synthetic construct
SEQUENCE: 7
ELKKFKLKLL SV                                                       12

SEQ ID NO: 8                moltype = AA   length = 13
FEATURE                     Location/Qualifiers
source                      1..13
                            mol_type = protein
                            organism = synthetic construct
SEQUENCE: 8
REGYGRIPRG ALL                                                      13

SEQ ID NO: 9                moltype = AA   length = 13
FEATURE                     Location/Qualifiers
source                      1..13
                            mol_type = protein
                            organism = synthetic construct
SEQUENCE: 9
DALDLTDKLV SFY                                                      13
```

```
SEQ ID NO: 10           moltype = AA   length = 10
FEATURE                 Location/Qualifiers
source                  1..10
                        mol_type = protein
                        organism = synthetic construct
SEQUENCE: 10
DQHRAALIAR                                                              10

SEQ ID NO: 11           moltype = AA   length = 11
FEATURE                 Location/Qualifiers
source                  1..11
                        mol_type = protein
                        organism = synthetic construct
SEQUENCE: 11
TNVEWLLDAL Y                                                            11

SEQ ID NO: 12           moltype = AA   length = 10
FEATURE                 Location/Qualifiers
source                  1..10
                        mol_type = protein
                        organism = synthetic construct
SEQUENCE: 12
DEQYQAVRAE                                                              10

SEQ ID NO: 13           moltype = AA   length = 12
FEATURE                 Location/Qualifiers
source                  1..12
                        mol_type = protein
                        organism = synthetic construct
SEQUENCE: 13
ELKKFKMKLL TV                                                           12

SEQ ID NO: 14           moltype = AA   length = 15
FEATURE                 Location/Qualifiers
source                  1..15
                        mol_type = protein
                        organism = synthetic construct
SEQUENCE: 14
QLREGYGRIP RGALL                                                        15

SEQ ID NO: 15           moltype = AA   length = 13
FEATURE                 Location/Qualifiers
source                  1..13
                        mol_type = protein
                        organism = synthetic construct
SEQUENCE: 15
DAIDLTDKLV SYY                                                          13

SEQ ID NO: 16           moltype = AA   length = 10
FEATURE                 Location/Qualifiers
source                  1..10
                        mol_type = protein
                        organism = synthetic construct
SEQUENCE: 16
DQHRQALIAR                                                              10

SEQ ID NO: 17           moltype = AA   length = 10
FEATURE                 Location/Qualifiers
source                  1..10
                        mol_type = protein
                        organism = synthetic construct
SEQUENCE: 17
TEVDGVLDAL                                                              10

SEQ ID NO: 18           moltype = AA   length = 10
FEATURE                 Location/Qualifiers
source                  1..10
                        mol_type = protein
                        organism = synthetic construct
SEQUENCE: 18
EGQYQAVRAE                                                              10

SEQ ID NO: 19           moltype = AA   length = 14
FEATURE                 Location/Qualifiers
source                  1..14
                        mol_type = protein
                        organism = synthetic construct
SEQUENCE: 19
```

```
DKMRKLFSFV PSWN                                                         14

SEQ ID NO: 20          moltype = AA  length = 14
FEATURE                Location/Qualifiers
source                 1..14
                       mol_type = protein
                       organism = synthetic construct
SEQUENCE: 20
KEIHPYLVMD LEQS                                                         14

SEQ ID NO: 21          moltype = AA  length = 13
FEATURE                Location/Qualifiers
source                 1..13
                       mol_type = protein
                       organism = synthetic construct
SEQUENCE: 21
AAAASVPAQS TAR                                                          13

SEQ ID NO: 22          moltype = AA  length = 4
FEATURE                Location/Qualifiers
source                 1..4
                       mol_type = protein
                       organism = synthetic construct
SEQUENCE: 22
GGGC                                                                     4

SEQ ID NO: 23          moltype = AA  length = 4
FEATURE                Location/Qualifiers
source                 1..4
                       mol_type = protein
                       organism = synthetic construct
SEQUENCE: 23
CGGG                                                                     4
```

COMPOSITIONS TARGETING APOPTOSIS-ASSOCIATED SPECK-LIKE PROTEIN WITH CASPASE ACTIVATION AND RECRUITMENT DOMAIN (ASC) AND METHODS OF USE

CROSS-REFERENCE TO RELATED APPLICATION

This application is a continuation of International Application No. PCT/US2023/031605, filed Aug. 31, 2023, which claims the benefit of U.S. Provisional Patent Application No. 63/402,601, filed Aug. 31, 2022, each of which is incorporated herein by reference in its entirety.

GOVERNMENT FUNDING

This invention was made with government support under NS083704 awarded by the National Institutes of Health. The government has certain rights in the invention.

SEQUENCE LISTING

This application contains a Sequence Listing electronically submitted via Patent Center to the United States Patent and Trademark Office as an xml file entitled "0310000175WO01.xml" having a size of 21 kilobytes and created on Aug. 30, 2023. The information contained in the Sequence Listing is incorporated by reference herein.

SUMMARY

This disclosure describes, in one aspect, an immunogen that includes an immunogenic carrier and an antigenic apoptosis-associated speck-like protein containing a caspase activation and recruitment domain (ASC) peptide linked to the immunogenic carrier. In one or more embodiments, the immunogenic carrier is a Qβ virus-like particle (VLP).

In one or more embodiments, the ASC peptide includes the amino acid sequence of SEQ ID NO:1 or an antigenic fragment thereof. In one or more of these embodiments, the antigenic fragment of SEQ ID NO: 1 includes SEQ ID NO:3, SEQ ID NO:4, SEQ ID NO:5, SEQ ID NO:6, SEQ ID NO:7, SEQ ID NO:8, SEQ ID NO:9, SEQ ID NO: 10, SEQ ID NO: 11, or SEQ ID NO:12.

In one or more embodiments, the immunogenic carrier is linked to the ASC peptide through a succinimidyl-6-[β-maleimidopropionamido] hexanoate (SMPH) cross-linker molecule.

In one or more embodiments, the immunogen further includes a second antigenic ASC peptide. In one or more of these embodiments, both ASC peptides are displayed on the same VLP.

In another aspect, this disclosure describes compositions that include an immunogen that includes an immunogenic carrier and an ASC peptide linked to the immunogenic carrier.

In one or more embodiments, the composition can include a first population of VLPs displaying a first antigenic ASC peptide, and a second population of VLPs displaying the second antigenic ASC peptide.

In one or more embodiments, the composition can further include an adjuvant.

In one or more embodiments, the composition is a vaccine.

In another aspect, this disclosure describes a method of treating an inflammatory condition in a subject. Generally, the method includes administering a therapeutically effective amount of a composition to the subject wherein the composition includes an immunogen that includes an immunogenic carrier and an antigenic ASC peptide linked to the immunogenic carrier.

In one or more embodiments, the method further includes administering to the individual at least one additional therapeutic agent for treating an inflammatory condition. In one or more of these embodiments, the immunogen includes a second antigenic ASC peptide. In one or more of these embodiments, both antigenic ASC peptides are linked to a single carrier.

In one or more embodiments, the composition includes a first population of immunogens and a second population of immunogens. The first population of immunogens includes a first population of immunogenic carriers and a first antigenic ASC peptide linked to the first population of immunogenic carriers. The second population of immunogens includes a second a second population of immunogenic carriers and a second ASC peptide linked to the second population of immunogenic carriers.

In one or more embodiments, at least one antigenic ASC peptide includes the amino acid sequence of SEQ ID NO: 1 or an antigenic fragment thereof. In one or more of these embodiments, the antigenic fragment of SEQ ID NO: 1 includes SEQ ID NO:3, SEQ ID NO:4, SEQ ID NO:5, SEQ ID NO:6, SEQ ID NO:7, SEQ ID NO:8, SEQ ID NO:9, SEQ ID NO: 10, SEQ ID NO:11, or SEQ ID NO:12.

In one or more embodiments, the composition is administered to the individual before the individual manifests a symptom or clinical sign of an inflammatory condition.

In another aspect, this disclosure describes a nucleic acid encoding an immunogen that includes an immunogenic carrier and an antigenic ASC peptide linked to the immunogenic carrier.

In another aspect, this disclosure describes an expression vector that includes a nucleic acid encoding an immunogen that includes an immunogenic carrier and an antigenic ASC peptide linked to the immunogenic carrier.

In another aspect, this disclosure describes a host cell that includes an expression vector that includes a nucleic acid encoding an immunogen that includes an immunogenic carrier and an antigenic ASC peptide linked to the immunogenic carrier.

The above summary is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Figure 1:
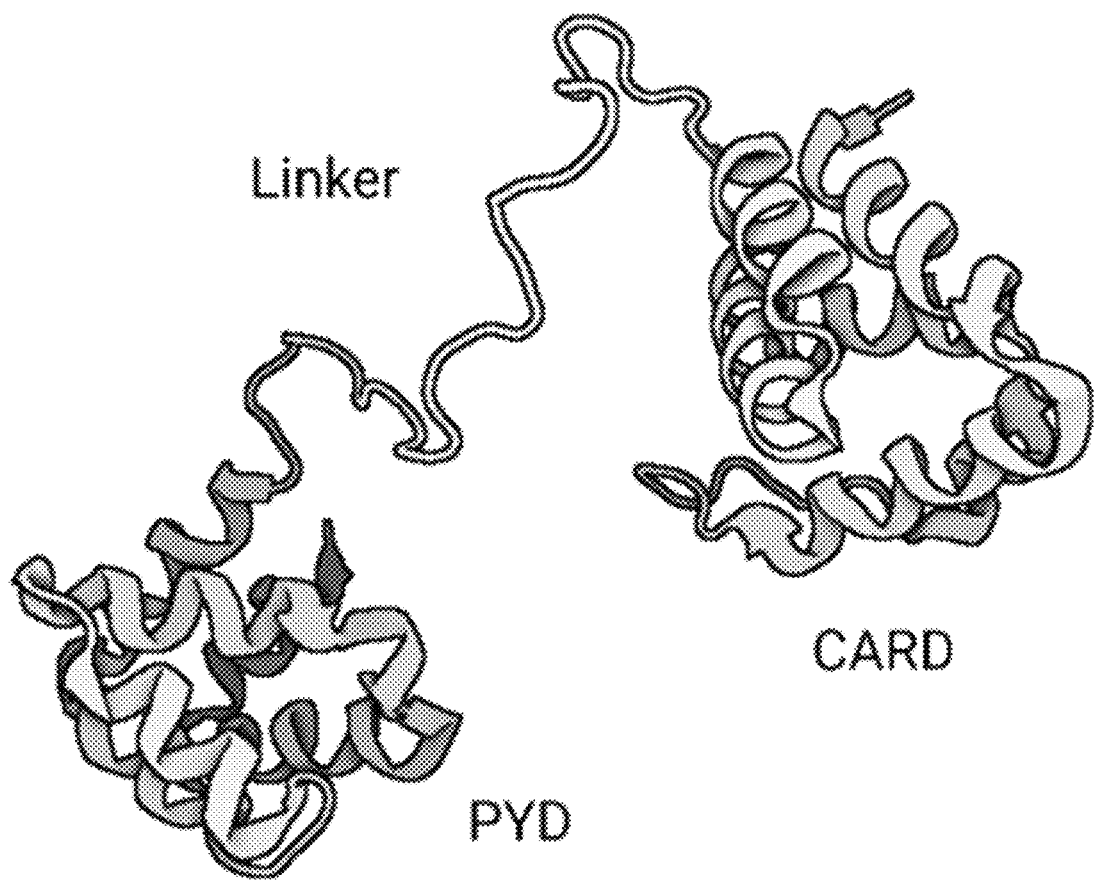
FIG. 1. Structure of the apoptosis-associated speck-like protein containing a caspase activation and recruitment domain (ASC) protein. ASC includes three domains: a pyrin domain (pyr), a flexible semi-structured linker region (linker), and a caspase activation and recruitment domain (CARD).

This disclosure describes compositions and methods that target apoptosis-associated speck-like protein containing a caspase activation and recruitment domain (ASC), which is also sometimes referred to in the scientific literature by the name of the gene that encodes the protein, PYCARD. The compositions can be used to treat inflammatory conditions by targeting the inflammasome.

The inflammasome is an innate immune complex capable of sensing a range of pathogen-associated molecular patterns (PAMPs) and damage-associated molecular patterns (DAMPs). The canonical inflammasome initiates an inflammatory signaling cascade mediated by the maturation of interleukin-1β and interleukin-18 by caspase-1. Inflammasomes are implicated in many disease states and often contribute to a protracted cytotoxic inflammatory state in many diseases characterized by chronic inflammation, including Alzheimer's disease. While there are several different inflammasome complexes that respond to different PAMPs and DAMPs, the apoptosis-associated speck-like protein containing a caspase activation and recruitment domain (ASC) protein is a common component of most inflammasomes and is a component of the ASC speck, a large protein complex that serves as a signal amplification platform for enhanced inflammasome activity.

Alzheimer's disease (AD) is a leading cause of death worldwide. There is currently no treatment that has been shown to prevent or cure AD. Four pathological hallmarks of AD within the brain include accumulation of extracellular amyloid β protein aggregates, accumulation of intracellular tau protein aggregates, low-level chronic neuroinflammation, and wide-spread neuronal degeneration resulting in memory loss and cognitive impairments. Therapeutic approaches have largely ignored the role of chronic neuroinflammation in disease progression. The NLRP3 inflammasome/ASC speck signaling complex, derived from inflammatory microglia, is a mediator of the chronic inflammatory state in the AD brain. Genetic knockout of either the NLRP3 or ASC genes reduce AD disease pathology in animal models.

This disclosure describes novel vaccine compositions against the NLRP3 inflammasome/ASC speck signaling complex. The compositions described herein generate a neutralizing antibody response that reduces neuroinflammation and inhibits disease progression in AD. The compositions include a virus-like particle (VLP) vaccine platform (e.g., a Qβ-based VLP platform) for the antigenic display of short peptide sequences from the apoptosis-associated speck-like protein containing a caspase activation and recruitment domain (ASC) protein that is a component of the NLRP3 inflammasome/ASC speck.

The amino acid sequence of human ASC protein is reflected in SEQ ID NO: 1. The human ASC protein includes a pyrin domain (amino acids 1-91 of SEQ ID NO:1) and a caspase activation and recruitment domain (CARD) domain (amino acids 107-195 of SEQ ID NO:1). The amino acid sequence of mouse ASC protein is reflected in SEQ ID NO:2. The mouse ASC protein includes a pyrin domain (amino acids 1-91 of SEQ ID NO:2) and a caspase activation and recruitment domain (CARD) domain (amino acids 105-193 of SEQ ID NO:2). Human ASC protein exists in at least three isoforms. Isoform 1 is shown in SEQ ID NO: 1 and the canonical form having 195 amino acid residues. Isoform 2 has 176 amino acid residues: amino acids 1-92 and 112-195 of SEQ ID NO:1—i.e., SEQ ID NO:1 with amino acids 93-111 excised. Isoform 3 has 135 amino acid residues: amino acids 1-25 and 86-195—i.e., SEQ ID NO: 1 with amino acids 26-85 excised. Isoform 1 and isoform 2 are considered the active isoforms of ASC. Isoform 3 binds to Caspase-1 and has a somewhat inhibitory function.

Figure 2:
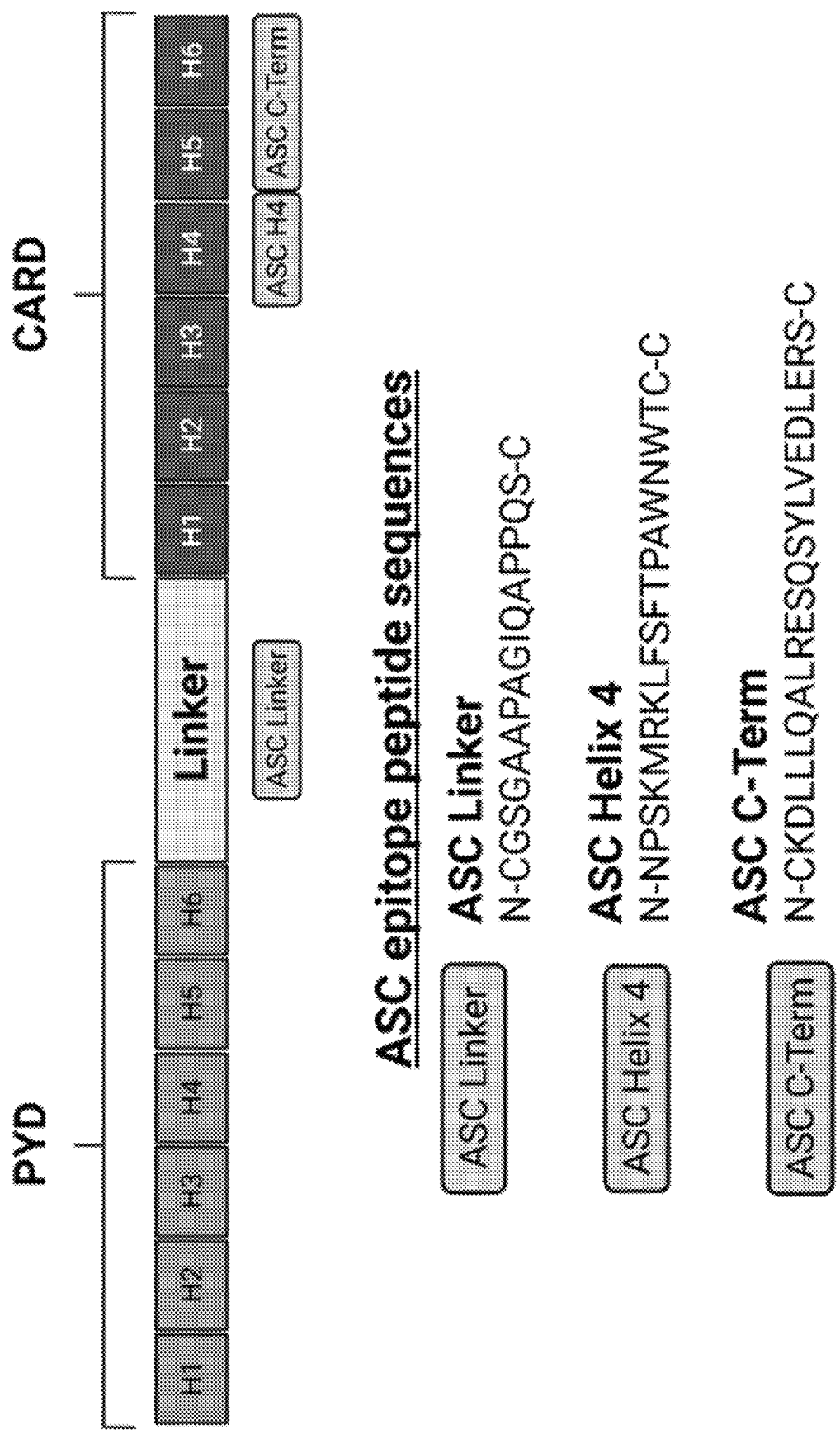
FIG. 2. Peptide sequences of ASC epitopes targeted for VLP development. Sequences are shown in the amino (N) terminus to carboxy (C) terminus orientation. The locations of the ASC epitopes are displayed with respect to the overall ASC protein structure. H1-6 represent the individual alpha helices within the PYD and CARD regions of the ASC protein. The N-terminal cysteine residue shown in the ASC Linker peptide sequence (SEQ ID NO:3) is an artifact of the conjugation method whereby a terminal cysteine residue is necessary for the conjugation reaction to occur. The other ASC epitopes included a terminal cysteine residue that was native to the protein. The remainder of the amino acid sequence shown in the immunogenic portion of SEQ ID NO:1 (amino acids 92-106 of SEQ ID NO:1). The amino acid sequences of the ASC Helix 4 (SEQ ID NO:4) immunogenic ASC peptide and the ASC C-Term (SEQ ID NO:5) immunogenic ASC peptide are shown.

Each vaccine included an ASC peptide conjugated to a Qβ bacteriophage virus-like particle (VLP). In one vaccine, referred to herein as the "ASC Linker" vaccine, the ASC peptide includes amino acids 92-106 of SEQ ID NO: 1 and targets the linker region between the pyrin domain and the CARD domain (FIG. 2). In a second vaccine, referred to herein as the "ASC Helix 4" vaccine, the ASC peptide includes amino acids 155-173 of SEQ ID NO: 1 and targets helix 4 of the CARD domain. In a third vaccine, referred to herein as the "ASC C-Term" vaccine, the ASC peptide includes amino acids 173-195 and targets the C-terminus of the CARD domain.

In the safety studies, animals received a two-injection vaccine regimen beginning at the age of two months with a booster vaccination three weeks after the first injection. The vaccine conditions included three different ASC peptide sequences conjugated to a Qβ bacteriophage VLP or a non-conjugated Qβ VLP sham treatment for a total of four treatment groups with five mice per group. Each of the ASC-VLP groups demonstrated significantly increased IgG titers against the ASC peptides compared to the sham vaccinated mice. There were no differences in survival rates or changes in animal weights between the ASC vaccinated groups and the sham vaccinated groups up to four months after vaccination. Complete blood cell counts and blood chemistry panels were also conducted for each mouse and showed no significant differences that would indicate severe disease or increased infections. These findings indicate that all three vaccines may be safe to use in various mouse models of disease, including Alzheimer's disease, for therapeutic intervention of inflammasome-mediated cytokine signaling in preclinical trials.

Excessive Interleukin-1 Signaling Contributes to Inflammatory Disease

Interleukin-1 (IL-1) is an inflammatory cytokine that plays a diverse role in health and disease as a major signaling component of the innate immune system. It is a master regulator of inflammation through several innate immune processes including its functions as a leukocytic pyrogen, leukocytic endogenous mediator and activating factor, activator of acute phase responses to infection and injury, and mediation of fever. Though IL-1 plays a protective role in response to infections and tissue injury in the acute response, dysregulated IL-1 signaling can contribute to various disease states including autoinflammatory diseases (e.g., cryopyrin-associated periodic syndromes, familial Mediterranean fever, etc.), metabolic syndromes (e.g., type 2 diabetes), excessive acute inflammation (e.g., sepsis), chronic inflammatory diseases (e.g., rheumatoid arthritis, chronic obstructive pulmonary disease, gout, Alzheimer's disease, etc.), and malignancy (e.g., HER2-negative breast cancer). The US Food and Drug Administration has approved several drugs directly targeting IL-1β signaling for the treatment of a wide array of inflammatory diseases. While targeting IL-1 signaling directly is sometimes effective for the management of several diseases, targeting the upstream production of IL-1 may be more effective.

Inflammasomes are Mediators of IL-1 Signaling

Figure 16:
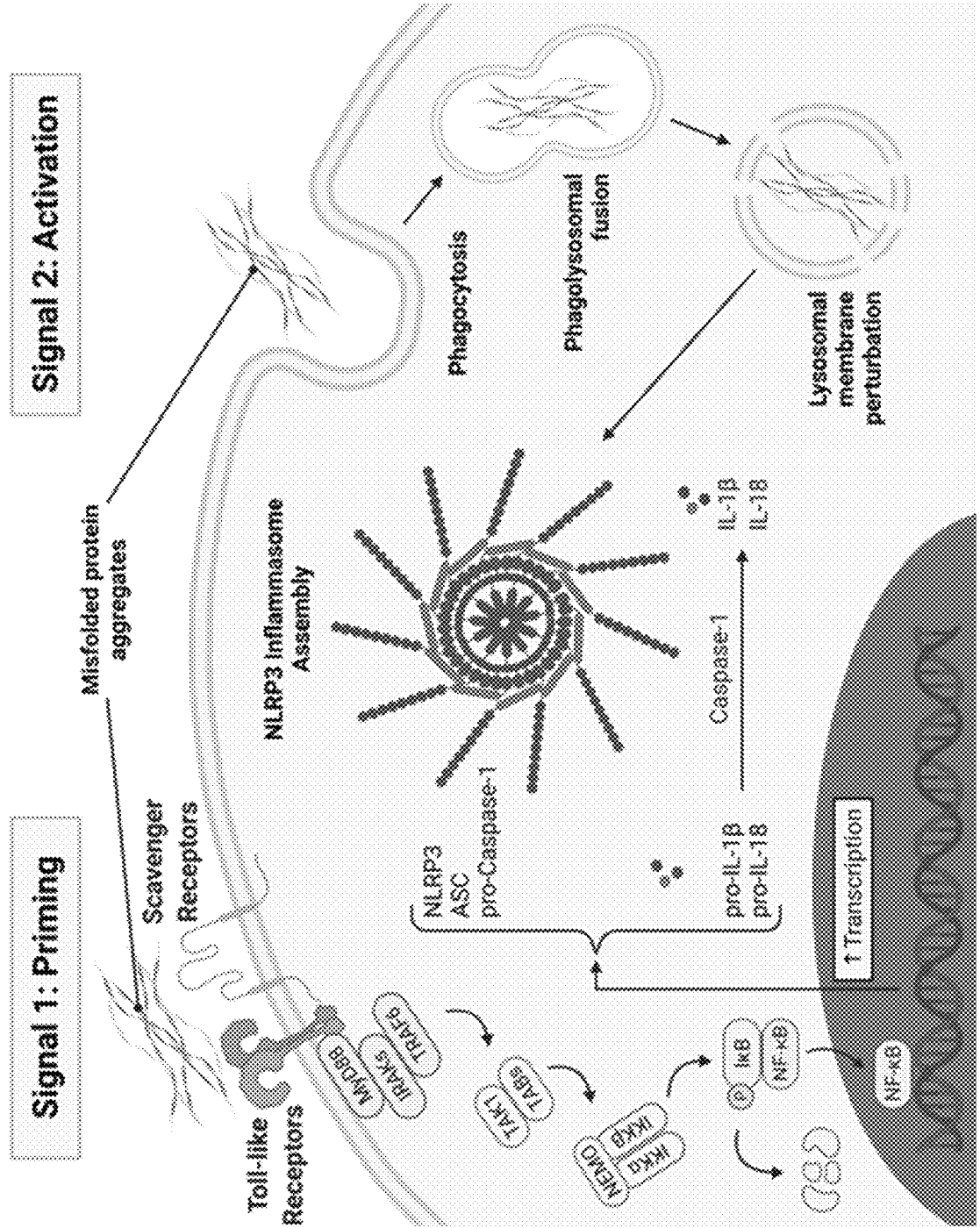
FIG. 16. Microglial NLRP3 inflammasome is primed and activated by AD protein aggregates. Illustration of cellular pathways involved in activating the inflammasome.
Figure 17:
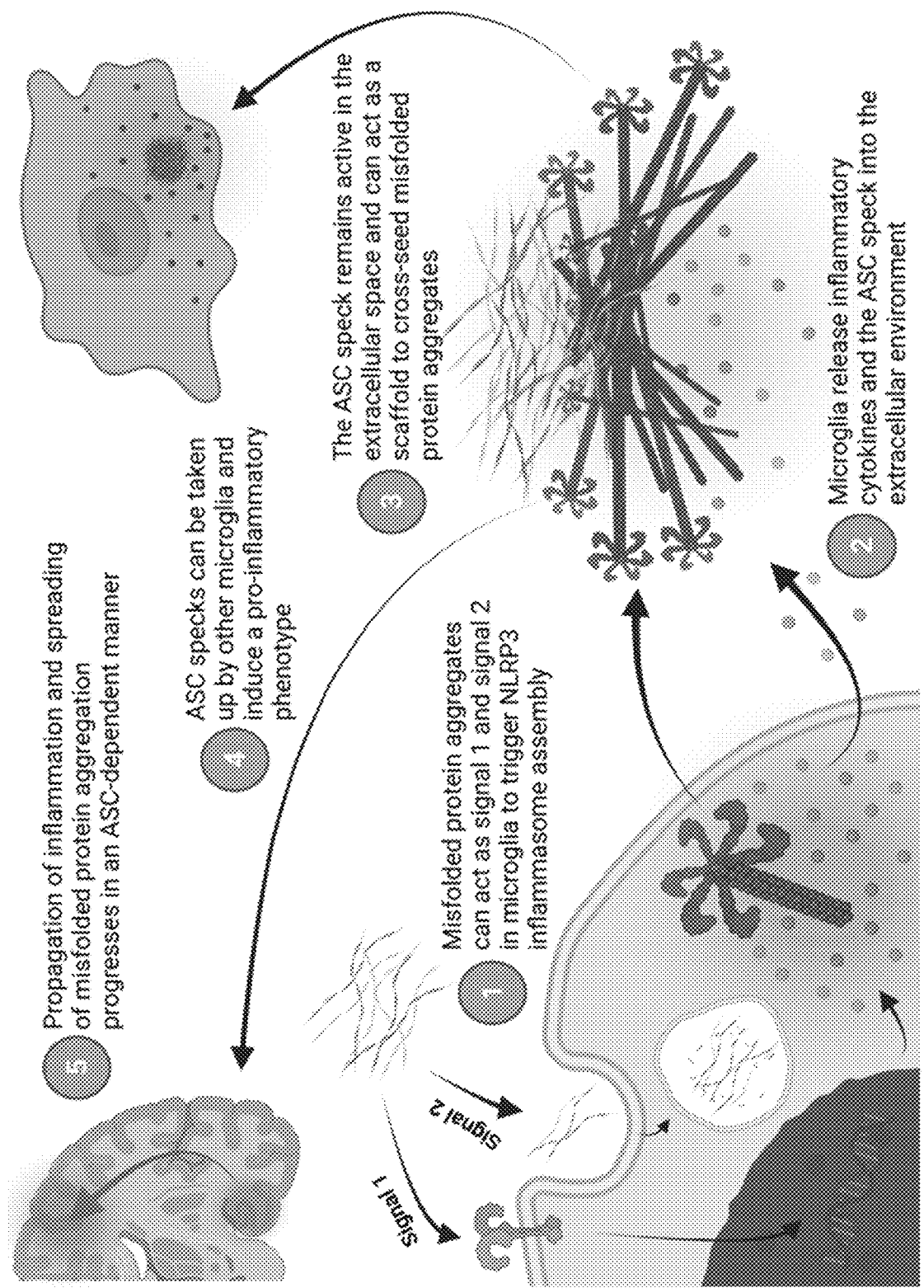
FIG. 17. Illustration of the ASC-dependent mechanism by which the inflammasome propagates inflammation and spread of misfolded protein aggregation.

Inflammasomes are innate immune signaling complexes that catalyze the maturation of IL-1 cytokines for inflammatory signaling. The NLRP3 inflammasome is a multiprotein oligomeric complex that includes nod-like receptor family pyrin domain containing 3 (NLRP3) protein, the apoptosis associated speck-like protein containing a caspase activation and recruitment domain (ASC) protein, and caspase-1 (FIG. 16). The ASC protein is a common component of numerous inflammasome types including the NLRP1, NLRP3, NLRP6, NLRP12, NLRC4, and AIM2 inflammasomes. Upon activation of the inflammasome, ASC can polymerize into large fibrils that may condense together into a large supramolecular complex called the ASC speck. The ASC speck is a ~1 micron in diameter protein complex that behaves as a signal amplification platform for enhanced IL-1 maturation.

NLRP3 Inflammasome-Mediated Interleukin-1β Signaling is Associated with Alzheimer's Disease and Other Neurodegenerative Diseases and May Drive Pathology Reactive microglia, the innate immune cells of the brain, drive tau pathology in animal models of Alzheimer's disease in an IL-1 dependent manner. This IL-1 signaling is primarily driven by NLRP3 inflammasome/ASC speck activity from microglia. Thus, therapeutics targeting inflammasome/ASC speck activity within the central nervous system may provide benefit for the treatment of Alzheimer's disease and other neurodegenerative disorders. Previously immunotherapies for treating Alzheimer's Disease involve vaccines that target tau protein using a virus-like particle (VLP) platform. These VLPs generate a robust antibody response against pathological tau protein aggregates and cleared these aggregates from the brain, resulting in improved memory and cognition in rodent models of Alzheimer's disease. VLPs provide an advantage over monoclonal antibody immunotherapy because they are non-expensive and simple to develop and do not require frequent re-dosing throughout the lifetime of the individual. This disclosure describes a similar technique using VLP technology applied against the inflammasome/ASC speck for the treatment of inflammatory diseases including Alzheimer's disease.

VLP Display

Many viral structural proteins have an intrinsic ability to self-assemble into virus-like particles (VLPs), which structurally resemble the virus from which they were derived but, because they lack viral genomes, they are absolutely non-infectious. VLPs not only can serve as stand-alone vaccines, but because their particulate nature and multivalent structure provoke strong immune responses, they can be used as platforms to enhance the immunogenicity of heterologous antigenic targets. For example, when short immunogenic peptides are displayed in a highly repetitive, multivalent fashion on VLPs, peptide-specific B cells are strongly activated, leading to high-titer, long-lasting antibody responses. VLPs derived from diverse virus types can serve as effective platforms for antigen display. The immunogens described herein are based on VLPs derived from a family of related single-stranded RNA bacteriophages, including MS2, PP7, AP205, and Qβ. These VLPs can be produced by expressing a single viral structural protein, called coat, from a plasmid in a bacterium. Peptides may be displayed on a VLP by bioconjugation techniques using cross linker molecules. In one or more embodiments, a peptide may be displayed on a VLP by conjugating the peptide to the VLP through a succinimidyl-6-[β-maleimidopropionamido] hexanoate (SMPH) cross-linker molecule. This technique results in VLPs that display target peptides at high valency, usually 180-360 peptides per VLP, and confers strong immunogenicity to displayed immunogenic peptides.

VLP-Based Vaccines Against Inflammasome-Mediated Inflammatory Diseases

This vaccine technology has therapeutic potential for the treatment of a variety of inflammatory diseases including, but not limited to, autoinflammatory diseases, metabolic syndromes, acute inflammation, chronic inflammatory diseases, malignancy, and neurodegenerative diseases such as Alzheimer's disease.

Figure 3:
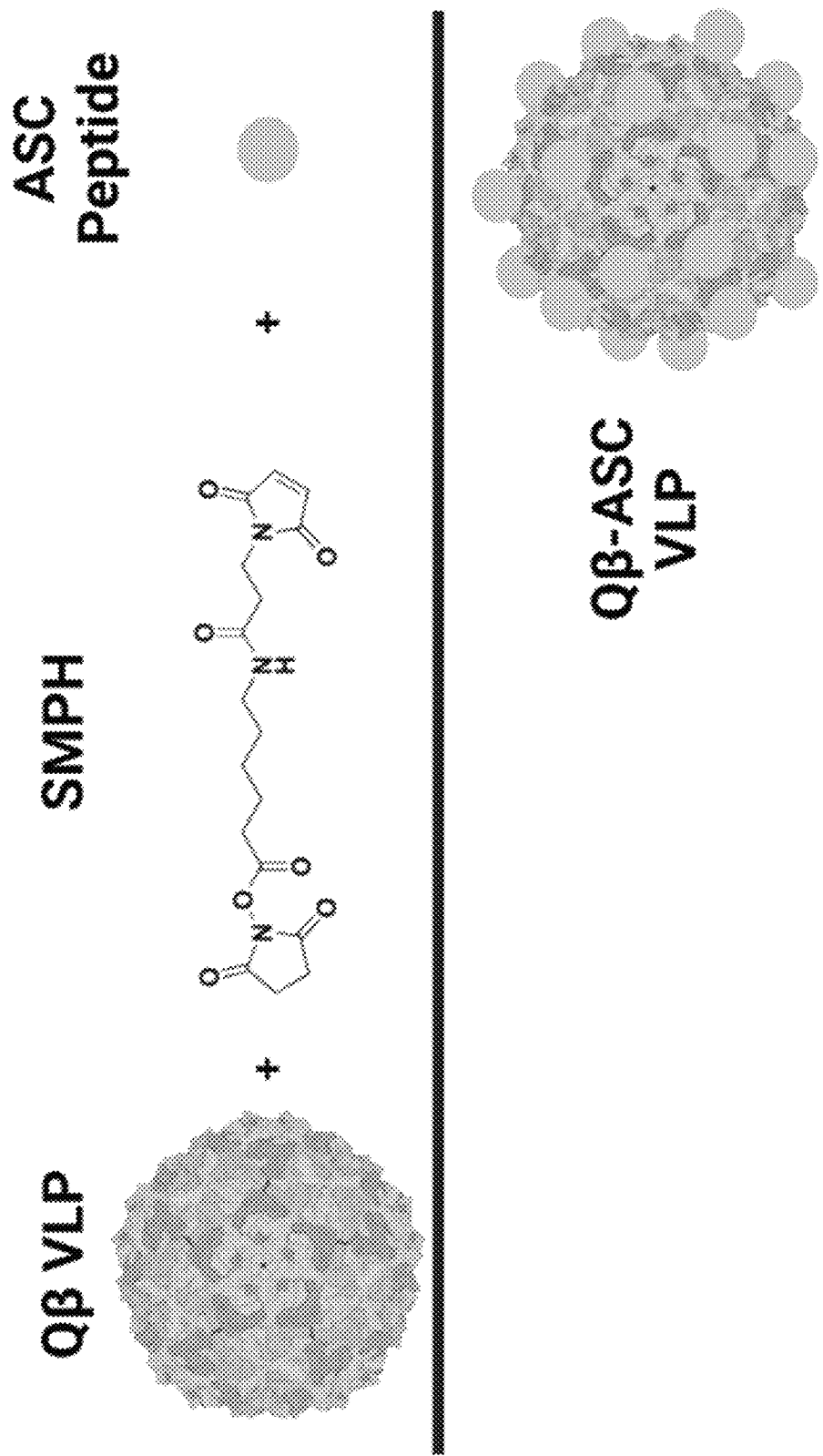
FIG. 3. Qβ bacteriophage coat proteins spontaneously self-assemble into a virus-like particle (VLP). Succinimidyl-6-[β-maleimidopropionamido] hexanoate (SMPH) is a bifunctional crosslinker that chemically conjugates ASC peptides to surface exposed lysine residues on Qβ monomers. The final product is a Qβ VLP displaying ASC peptides in a highly repetitive multivalent manner.

Exemplary embodiments of ASC-targeting vaccines target epitopes on the ASC protein (FIG. 1). The epitopes that have been targeted include the flexible linker sequence, alpha helix 4 from the CARD region, and the C-terminus region containing alpha helix 5 and 6 from the CARD region (FIG. 2). In one or more alternative exemplary embodiments, other epitopes may be targeted. Qβ bacteriophage coat proteins that spontaneously self-assemble into a VLP were used as the antigen display platform and were chemically conjugated to the ASC epitope peptide sequences using succinimidyl-6-[β-maleimidopropionamido] hexanoate (SMPH) as a chemical cross-linker (FIG. 3). The final products are Qβ VLPs displaying ASC peptide epitopes in a multivalent, highly repetitive manner capable of inducing strong B cell responses for the production of high affinity antibodies against the ASC epitope antigen.

Figure 4:
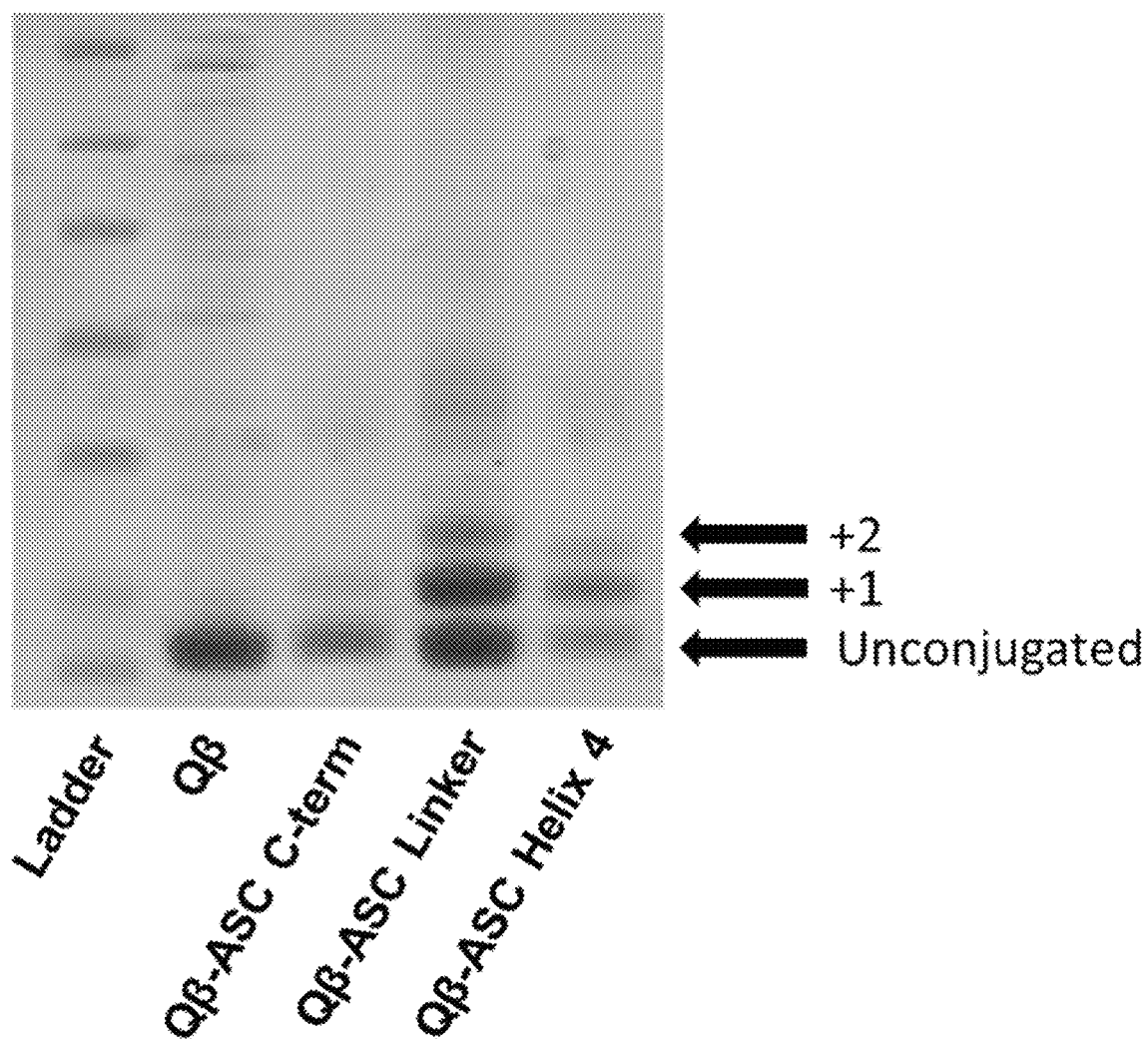
FIG. 4. Mobility shift gel electrophoresis of Qβ and Qβ conjugated to the ASC Linker, Helix 4, and C-term peptides indicating a successful conjugation reaction for VLP synthesis.

While FIG. 3 illustrates an exemplary embodiment in which the VLP displays a single ASC peptide in a multivalent manner (i.e., the VLP displays a plurality of copies of a single ASC peptide), the vaccine may be designed so that the VLP displays more than one ASC peptide. In one more embodiments, therefore, the VLP may display one, two, three, or more different ASC peptides. Efficiency of peptide conjugation on the VLP can be evaluated using any conventional method such as, for example, mobility shift gel electrophoresis. FIG. 4 shows mobility shift of Qβ towards higher molecular weights according to the number of ASC peptides that have successfully conjugated to the Qβ monomer.

Figure 6:
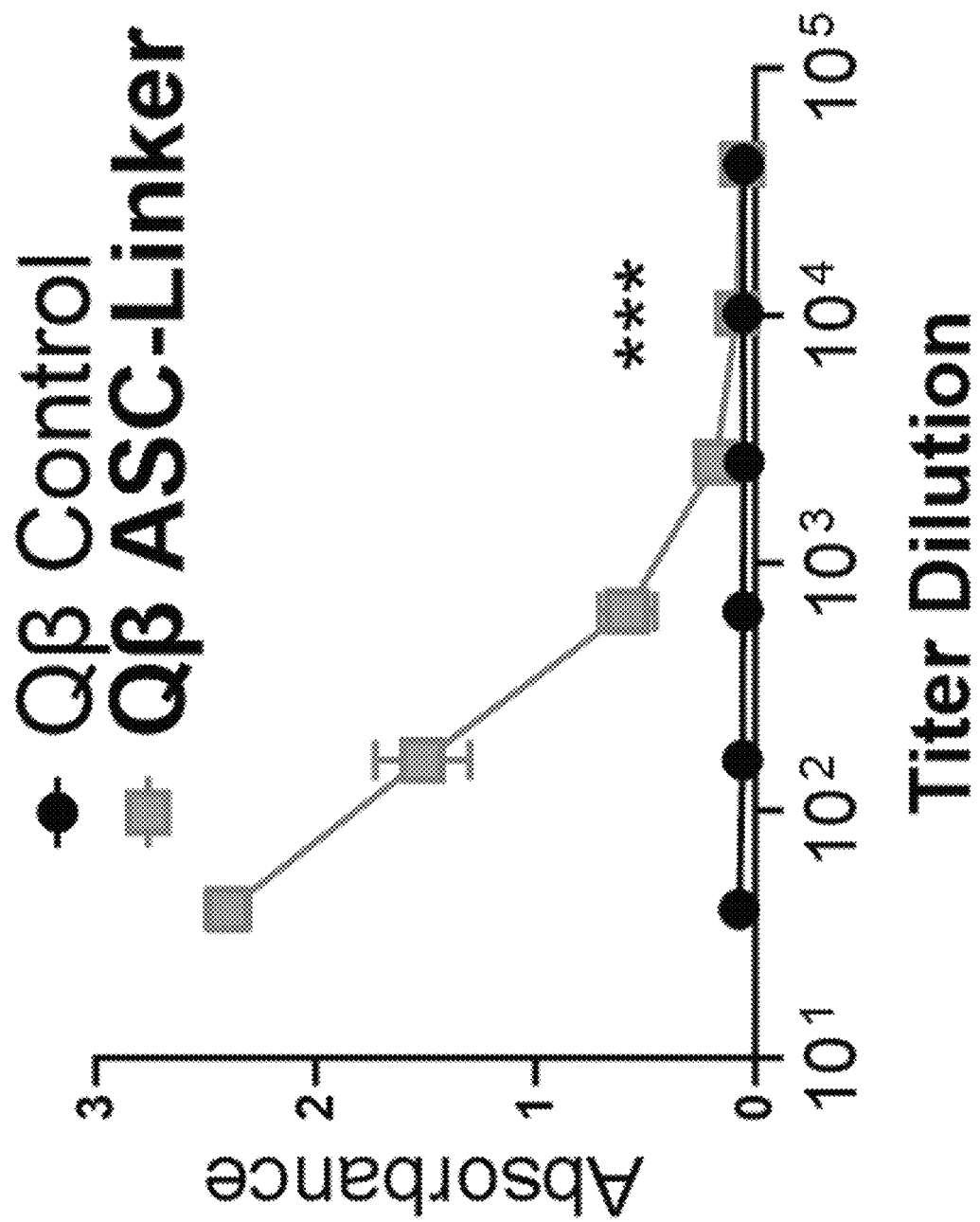
FIG. 6. Dilution curve of immune sera from mice vaccinated with the Qβ ASC-Linker construct, indicating generation of an antibody response.
Figure 7:
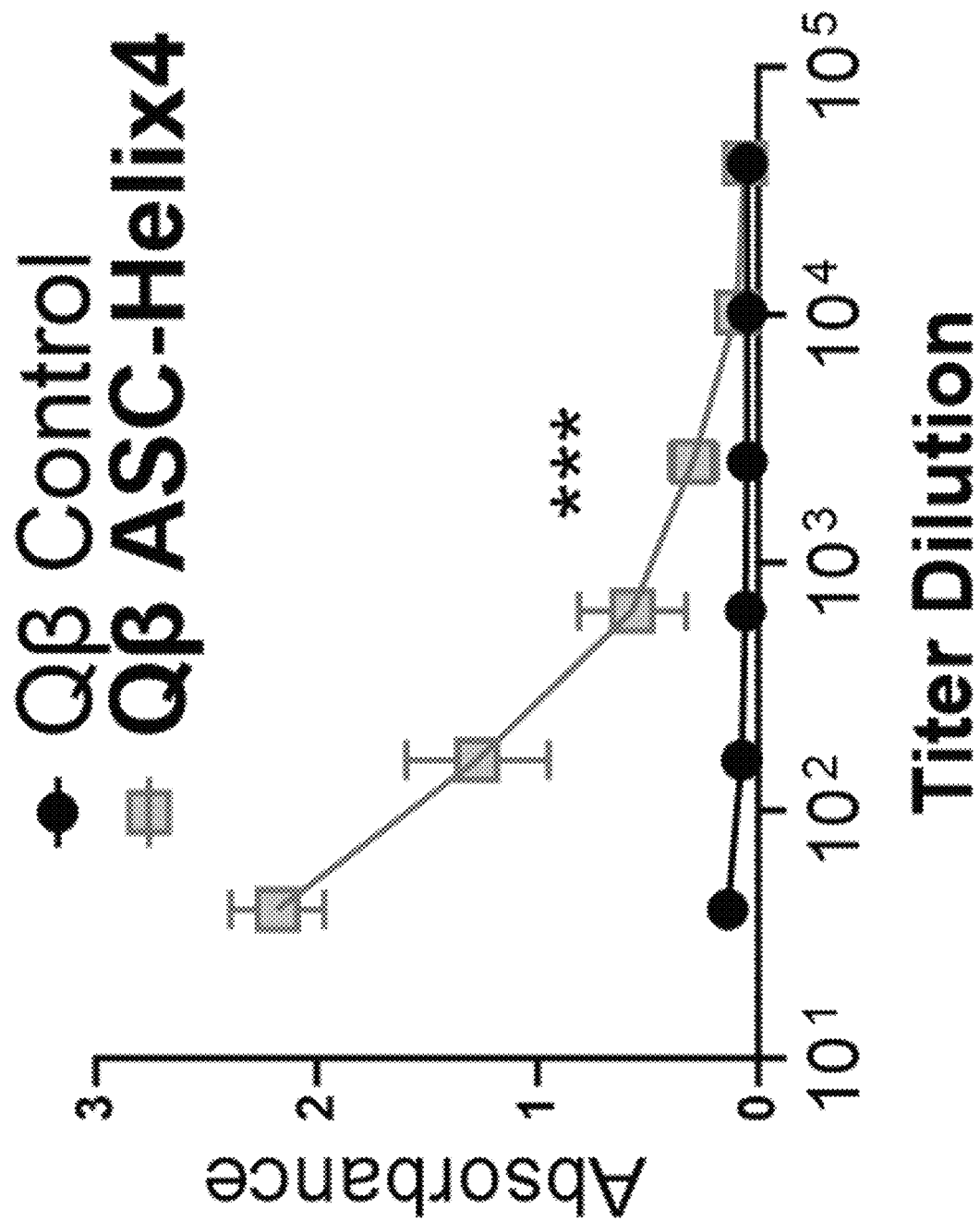
FIG. 7. Dilution curve of immune sera from mice vaccinated with the Qβ ASC-Helix 4 construct, indicating generation of an antibody response.
Figure 8:
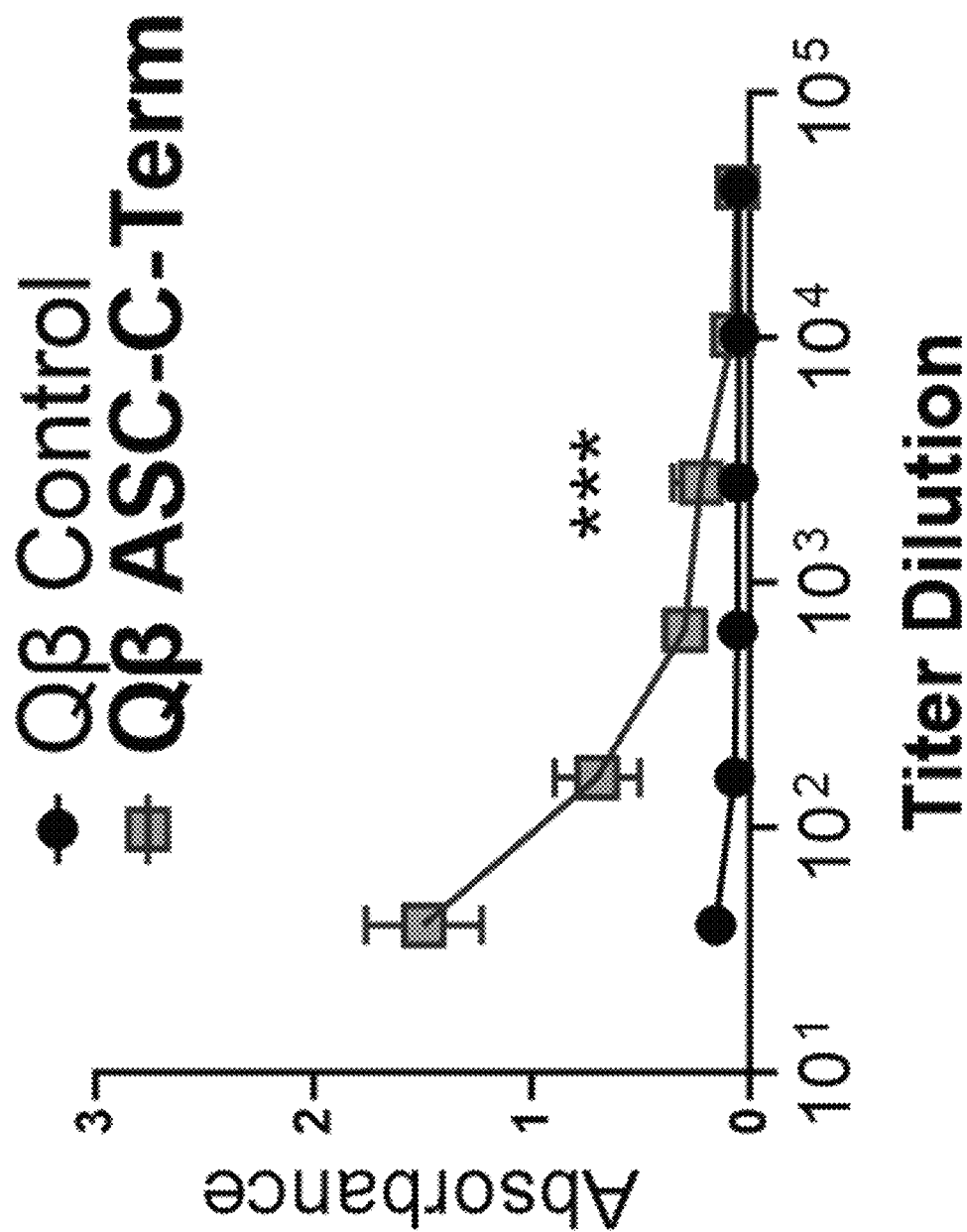
FIG. 8. Dilution curve of immune sera from mice vaccinated with the Qβ ASC-C Term construct, indicating generation of an antibody response.

Once produced, one can immunize a subject using the ASC-VLP composition. Immunogenicity of a given ASC-VLP vaccine composition can be evaluated using any conventional method such as, for example, an enzyme-linked immunosorbent assay (ELISA). The ASC Linker, ASC Helix 4, and ASC C-Term VLPs are immunogenic and elicit high-titer IgG antibody responses. FIGS. 6-8 show data demonstrating the immunogenicity of the ASC Linker (FIG. 6), ASC Helix 4 (FIG. 7), and ASC C-Term (FIG. 8) VLPs.

Figure 5:
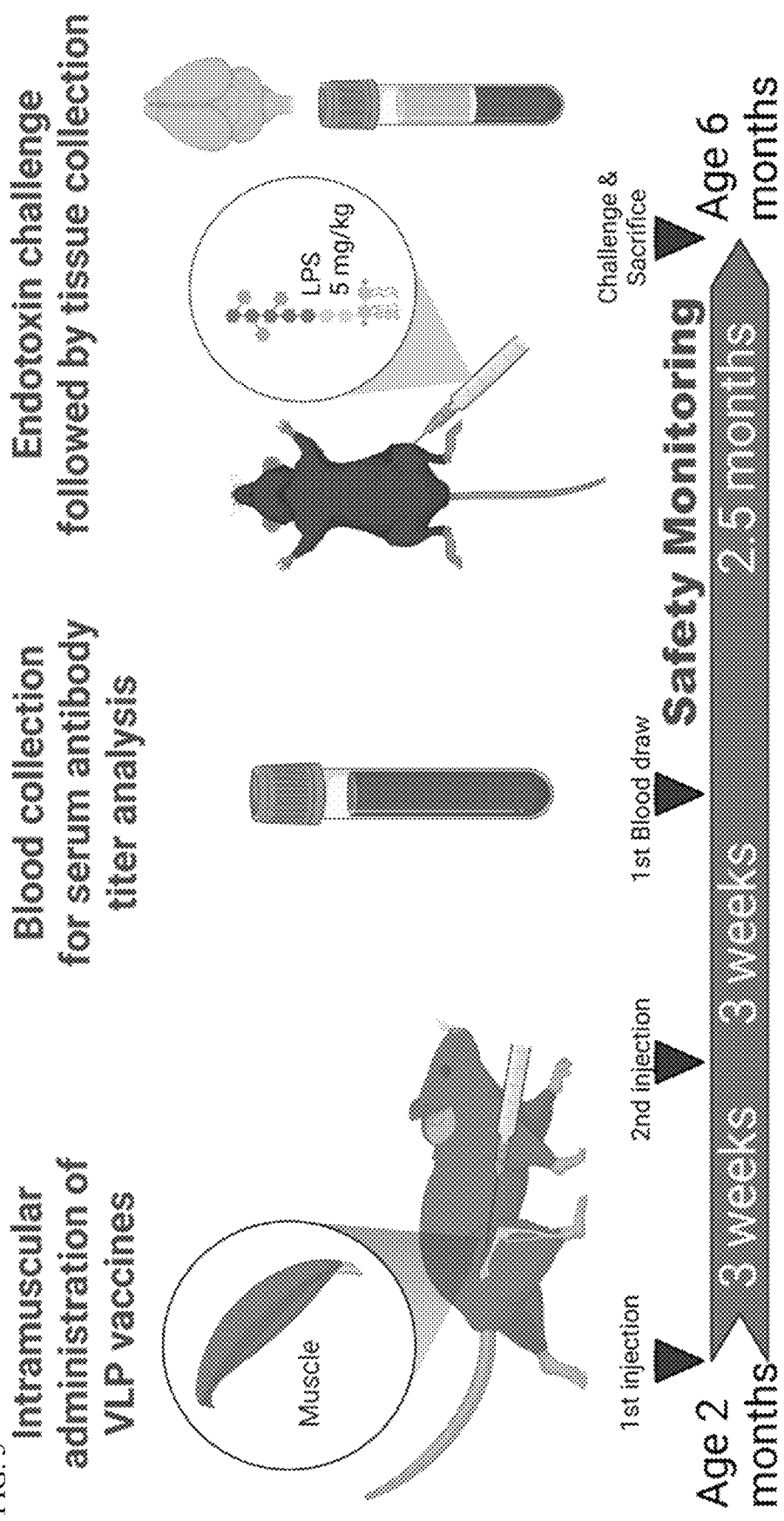
FIG. 5. Schematic of experimental timeline for all preliminary data. Animals were vaccinated at two months of age with Qβ Control or Qβ-ASC VLP vaccines with two doses spaced three weeks apart. Three weeks after the second vaccination, blood samples were collected for antibody titer analysis and used for antibody reactivity experiments with human and mouse brain tissue. Safety monitoring was conducted for an additional 2.5 months. At six months of age, endpoint blood samples were collected for blood cell counts and blood biochemistry profiling. The animals were then injected with 5 mg/kg lipopolysaccharide to induce a systemic inflammatory response. Animals were sacrificed nine hours later and serum and brain tissues were collected for profiling of inflammasome activation.

Safety of a given ASC-VLP vaccine composition can be evaluated by monitoring (e.g., for a period of six-months) immunized subjects for adverse health effects. Subjects may be monitored using, for example, complete blood cell count profiles, basic blood chemistry panels, changes in weight, and survival. FIG. 5 provides a schematic illustration of an experimental timeline for all preliminary data. The experimental timeline in FIG. 5 depicts that safety monitoring was conducted for an additional 2.5 months after the VLP vaccine injection doses and after the first blood draw was collected.

Figure 9:
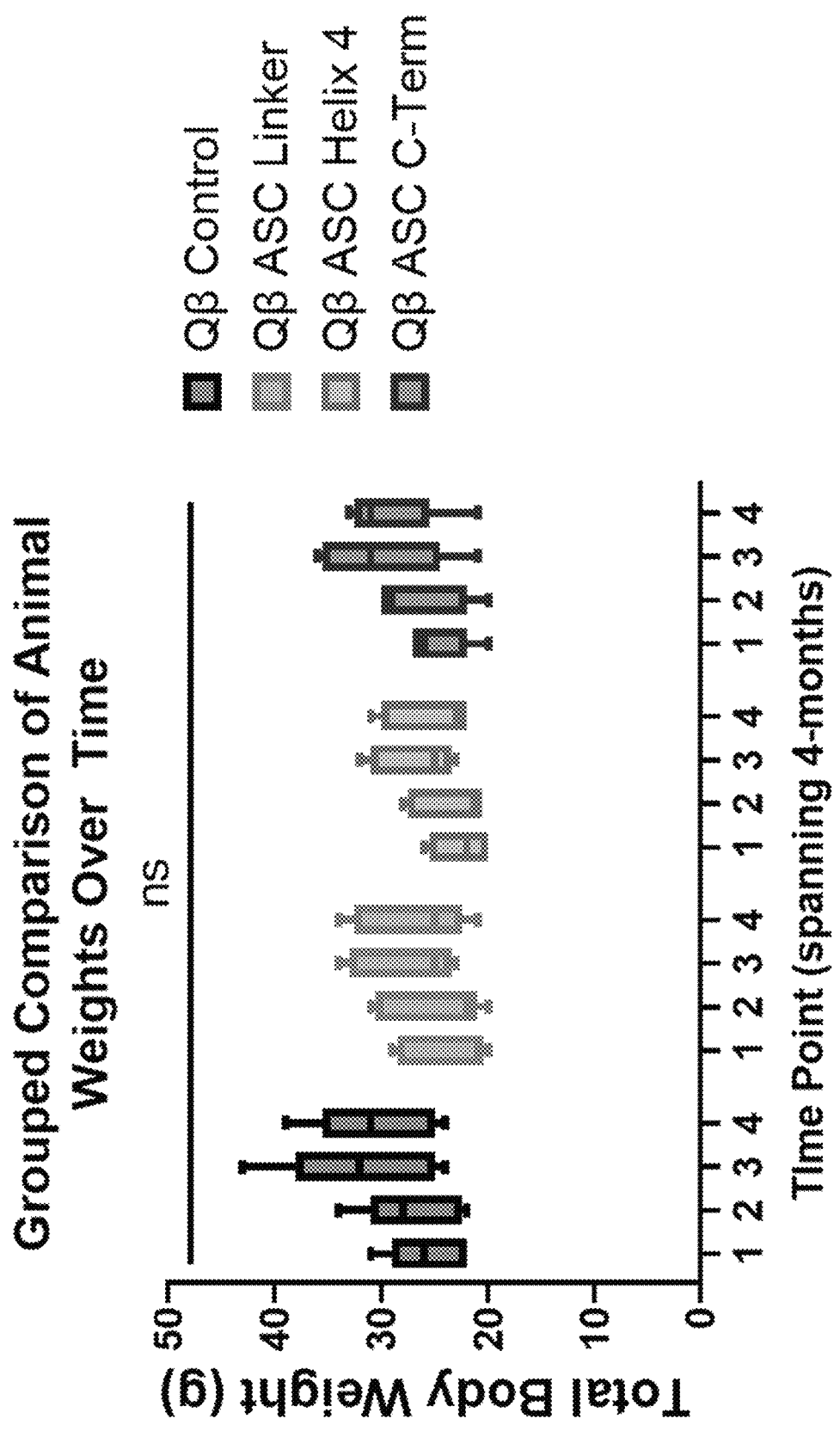
FIG. 9. Total body weights of Qβ Control and Qβ-ASC VLP vaccinated animals over a 4-month time period. There is no difference in animal weights between treatment groups and the control at any time point indicating Qβ-ASC VLP vaccination was well tolerated.
Figure 10:
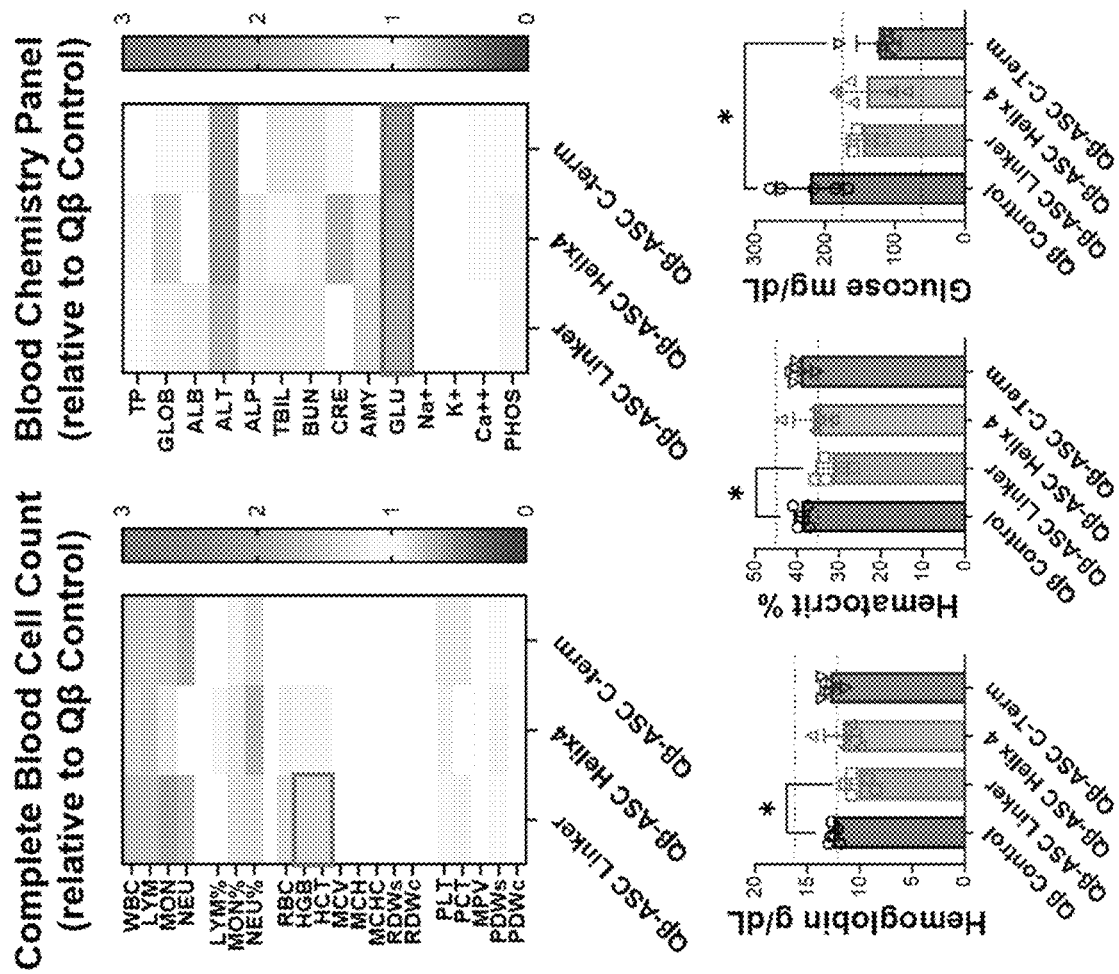
FIG. 10. Complete blood cell counts and blood biochemistry panel of Qβ-ASC VLP vaccinated mice relative to Qβ Control at four months post vaccination with outlined boxes indicating statistically significant differences (p<0.05, one-way ANOVA) from Qβ Control and individual graphs for all statistically significant findings with normal reference ranges shown by dotted lines. Overall the Qβ-ASC VLP vaccines were well tolerated. There are no differences in immune cell counts/percent between treatment groups and the Qβ Control group. The Qβ-ASC Linker vaccine is associated with mild anemia but there are no differences in red blood cell parameters for the other Qβ-ASC VLP vaccinated groups and the control group. There are no differences in platelet characteristics between the Qβ-ASC VLP vaccinated groups and the control group. There are no changes in multiple markers of organ function assessed by a basic blood biochemistry panel. Qβ Control vaccinated mice developed high blood glucose levels indicative of diabetes while Qβ-ASC VLP vaccinated mice maintained normal blood glucose levels.

For example, FIG. 9 shows data demonstrating that the ASC Linker vaccine, the ASC Helix 4 vaccine, and the ASC C-Term vaccine were well tolerated, with no vaccine causing significant weight loss compared to sham vaccination with Qβ VLP lacking any ASC peptides. Similarly, FIG. 10 shows complete blood count profiles demonstrating that all of the vaccines were well tolerated with mild anemia (e.g., low hemoglobin and hematocrit) only occurring with the ASC Linker vaccine. FIG. 10 also shows a basic blood chemistry panel that further demonstrates that all vaccines were well tolerated with no markers of organ damage or dysfunction.

Efficacy of the ASC-VLP vaccine composition can be evaluated using any suitable measure of inflammasome activity. In the exemplary context of Alzheimer's Disease, an exemplary model designed to measure cognitive ability may be used. For example, healthy C57Bl6/J mice can be hippocampally injected with brain lysates from human AD patients or with a PBS vehicle. The animals can then be further subdivided into a group receiving ASC-VLP vaccination and a sham vaccine treatment. After a predetermined period of time (e.g., two months in some exemplary models), the animals can be subjected to a battery of cognitive behavioral tasks and then sacrificed for histological and biochemical analyses of disease pathology and inflammatory markers.

Metabolic disorders such as Type 2 diabetes have been linked to inflammasome activity as a potential risk factor. FIG. 10 demonstrates that mice that received sham vaccination with Qβ VLP lacking any ASC peptides developed high blood glucose levels indicative of diabetes while ASC-VLP vaccinated animals all maintained healthy blood glucose levels. This was an exploratory finding that indicates another possible exemplary model for measuring efficacy of ASC-VLP vaccination in an inflammasome mediated disease condition.

Thus, this disclosure describes compositions and methods that provides state-of-the-art immunotherapy approach that targets proteins responsible for damaging inflammation. The compositions described herein target inflammasome-related proteins and inflammatory cytokines. In one or more embodiments, the compositions and methods described herein induce antibody production with minimal induction of severe inflammatory response. Accordingly, the compositions and methods may be appropriate for use in treating inflammatory conditions including, but not limited to, Alzheimer's Disease. A vaccine targeting ASC reduces neuroinflammation and disease pathology in an animal model of AD. The NLRP3 inflammasome contributes to the pathological tau aggregation process through regulation of kinase/phosphatase activity by inflammatory signals and can be targeted to reduce ptau burden.

The compositions include a VLP-based immunogen that includes an antigenic ASC peptide (also referred to herein as a "an ASC-targeting peptide") such as, for example, the amino acids of SEQ ID NO:1, SEQ ID NO:2, or an immunogenic fragment thereof. Exemplary immunogenic ASC peptide fragments include, but are not limited to, any one of SEQ ID NO:3, SEQ ID NO:4, SEQ ID NO:5, SEQ ID NO:6, SEQ ID NO: 7, SEQ ID NO:8, SEQ ID NO:9, SEQ ID NO:10, SEQ ID NO:11, SEQ ID NO: 12, SEQ ID NO:13, SEQ ID NO: 14, SEQ ID NO:15, SEQ ID NO: 16, SEQ ID NO: 17, SEQ ID NO: 18, SEQ ID NO:19, SEQ ID NO:20, SEQ ID NO:21, or an immunogenic fragment of any of the foregoing. Further, the immunogen can include a VLP that displays more than one population of antigenic ASC peptides—e.g., a first population of antigenic ASC peptides that includes the amino acids of a first ASC immunogenic peptide and a second population of antigenic ASC peptides that includes a second immunogenic ASC peptide. Thus, the immunogen can be designed to display one, two, three, four, five, six, or more antigenic ASC peptides.

In another aspect, an immunogenic composition may include more than one population of VLPs. For example, an immunogenic composition can include a first population of VLPs displaying a first antigenic ASC peptide and a second population of VLPs displaying a second antigenic ASC peptide. Still further, an immunogenic composition may include a first population of VLPs displaying one or more antigenic ASC peptides and a second population VLPs displaying one or more antigenic ASC peptides, with the number and identity of antigenic peptides displayed by the VLPs in the second population being independent of the number and identity of the antigenic peptides displayed by the first population of VLPs.

As used herein, an antigenic ASC peptide can refer to any ASC amino acid sequence that elicits an ASC-targeted immune response when introduced into an immunocompetent subject. Exemplary antigenic ASC peptides include peptides that include the amino acid sequence of any one or more of SEQ ID NO: 1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO: 10, SEQ ID NO: 11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, any immunogenic fragment of any of the foregoing, or any peptide that is structurally similar to any of the foregoing peptides or immunogenic fragments.

As used herein, a peptide is "structurally similar" to a reference polypeptide if the amino acid sequence of the peptide possesses a specified amount of identity compared to the reference peptide. Structural similarity of two peptides can be determined by aligning the residues of the two peptides (for example, a candidate polypeptide and any one of SEQ ID NOs:1-21) to optimize the number of identical amino acids along the lengths of their sequences; gaps in either or both sequences are permitted in making the alignment in order to optimize the number of identical amino acids, although the amino acids in each sequence must nonetheless remain in their proper order. A candidate peptide is the peptide being compared to the reference peptide (e.g., any one of SEQ ID NOs: 1-21). A candidate peptide can be isolated, for example, from an animal, or can be produced using recombinant techniques, or chemically or enzymatically synthesized.

A pair-wise comparison analysis of amino acid sequences can be carried out using the BESTFIT algorithm in the GCG package (version 10.2, Madison WI). Alternatively, peptides may be compared using the Blastp program of the BLAST 2 search algorithm, as described by et al., (*FEMS Microbiol Lett,* 174, 247-250 (1999)), and available on the National Center for Biotechnology Information (NCBI) website. The default values for all BLAST 2 search parameters may be used, including matrix=BLOSUM62; open gap penalty=11, extension gap penalty=1, gap x_dropoff=50, expect=10, wordsize=3, and filter on.

An antigenic ASC peptide can include amino acids in addition to any one of SEQ ID NOs:1-21, so long as the additional amino acids do not eliminate immunogenicity toward ASC. For example, an antigenic ASC peptide may have a linker region containing the amino acids GGGC (SEQ ID NO: 22) or CGGG (SEQ ID NO:23).

In the comparison of two amino acid sequences, structural similarity may be referred to by percent "identity" or may be referred to by percent "similarity." "Identity" refers to the presence of identical amino acids. "Similarity" refers to the presence of not only identical amino acids but also includes the presence of conservative substitutions. A conservative substitution for an amino acid in an immunogenic peptide as described herein may be selected from other members of the class to which the amino acid belongs. For example, it is well-known in the art of protein biochemistry that an amino acid belonging to a grouping of amino acids having a particular size or characteristic (such as charge, hydrophobicity, and hydrophilicity) can be substituted for another amino acid without altering the activity of a protein, particularly in regions of the protein that are not directly associated with biological activity. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine, and glutamine. The positively charged (basic) amino acids include arginine, lysine, and histidine. The negatively charged (acidic) amino acids include aspartic acid and glutamic acid. Conservative substitutions include, for example, Lys for Arg and vice versa to maintain a positive charge; Glu for Asp and vice versa to maintain a negative charge; Ser for Thr so that a free —OH is maintained; and Gln for Asn to maintain a free —NH₂. Likewise, biologically active analogs of a polypeptide containing deletions or additions of one or more contiguous or noncontiguous amino acids that do not eliminate a functional activity of the peptide are also contemplated.

Exemplary ASC-targeting peptides are provided in Table 1.

TABLE 1

| Human ASC Peptide Sequence | Region | SEQ ID NO: |
|---|---|---|
| GSGAAPAGIQAPPQS | Linker | 3 |
| NPSKMRKLFSFTPAWNWTC | Helix 4 | 4 |
| CKDLLLQALRESQSYLVEDLERS | CARD (H5-6) | 5 |
| MGRARDAILDALENL | PYD (H1) | 6 |
| ELKKFKLKLLSV | PYD (H2) | 7 |
| REGYGRIPRGALL | PYD (H3) | 8 |
| DALDLTDKLVSFY | PYD (H4) | 9 |
| DQHRAALIAR | CARD (H1) | 10 |
| TNVEWLLDALY | CARD (H2) | 11 |
| DEQYQAVRAE | CARD (H3) | 12 |

| Mouse ASC Peptide Sequence | Region | % Identity w/Human ASC | SEQ ID NO: |
|---|---|---|---|
| ELKKFKMKLLTV | PYD (H2) | 83.3 | 13 |
| QLREGYGRIPRGALL | PYD (H3) | 93.3 | 14 |

TABLE 1-continued

| | | | |
|---|---|---|---|
| DAIDLTDKLVSYY | PYD (H4) | 84.6 | 15 |
| DQHRQALIAR | CARD (H1) | 90.0 | 16 |
| TEVDGVLDAL | CARD (H2) | 66.7 | 17 |
| EGQYQAVRAE | CARD (H3) | 90.0 | 18 |
| DKMRKLFSFVPSWN | CARD (H4) | 84.6 | 19 |
| KEIHPYLVMDLEQS | CARD (H6) | 70.0 | 20 |
| AAAASVPAQSTAR | Linker | 46.0 | 21 |

Thus, in one or more embodiments, an ASC-targeting peptide as described herein can include a peptide (or peptide domain—i.e., a portion of a larger amino acid sequence) with at least 66%, at least 70%, at least 75%, at least 79%, at least 81%, at least 83%, at least 84%, at least 87%, at least 90%, at least 93%, or at least 96% sequence similarity to the amino acid sequence of any one of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO: 10, SEQ ID NO:11, SEQ ID NO: 12, SEQ ID NO:13, SEQ ID NO:14, SEQ ID NO:15, SEQ ID NO: 16, SEQ ID NO:17, SEQ ID NO:18, SEQ ID NO: 19, SEQ ID NO:20, or SEQ ID NO:21. Thus, in one or more embodiments, an ASC-targeting polypeptide that includes a domain corresponding to any one of SEQ ID NO:3-21, the portion of the ASC peptide that corresponds to SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO: 14, SEQ ID NO: 15, SEQ ID NO:16, SEQ ID NO:17, SEQ ID NO:18, SEQ ID NO:19, SEQ ID NO:20, or SEQ ID NO:21 can include a total of no more than six, no more than five, no more than four, no more than three, no more than two, or no more than one amino acid deletions, amino acid additions, and/or non-conservative amino acid substitutions compared to the reference ASC peptide sequence.

In one or more embodiments, an ASC-targeting peptide as described herein can include a peptide (or peptide domain—i.e., a portion of a larger amino acid sequence) with at least 66%, at least 70%, at least 75%, at least 79%, at least 81%, at least 83%, at least 84%, at least 87%, at least 90%, at least 93%, or at least 96% sequence identity to the amino acid sequence of any one of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO: 10, SEQ ID NO: 11, SEQ ID NO: 12, SEQ ID NO:13, SEQ ID NO: 14, SEQ ID NO: 15, SEQ ID NO: 16, SEQ ID NO: 17, SEQ ID NO:18, SEQ ID NO:19, SEQ ID NO:20, or SEQ ID NO:21. Thus, in one or more embodiments, an ASC-targeting polypeptide that includes a domain corresponding to any one of SEQ ID NO:3-21, the portion of the ASC peptide that corresponds to SEQ ID NO:3, SEQ ID NO:4, SEQ ID NO:5, SEQ ID NO:6, SEQ ID NO:7, SEQ ID NO:8, SEQ ID NO:9, SEQ ID NO: 10, SEQ ID NO:11, SEQ ID NO: 12, SEQ ID NO: 13, SEQ ID NO: 14, SEQ ID NO: 15, SEQ ID NO: 16, SEQ ID NO:17, SEQ ID NO: 18, SEQ ID NO: 19, SEQ ID NO:20, or SEQ ID NO:21 can include a total of no more than six, no more than five, no more than four, no more than three, no more than two, or no more than one amino acid deletions and/or amino acid additions compared to the reference ASC peptide sequence.

In one or more embodiments, an ASC-targeting peptide as described herein can be designed to provide an additional sequence, such as, for example, added C-terminal or N-terminal amino acids that can, for example, facilitate purification by trapping on columns or use of antibodies. Such tags include, for example, histidine-rich tags that allow purification of polypeptides on nickel columns. Such gene modification techniques and suitable additional sequences are well known in the molecular biology arts. Alternatively or additionally, an additional amino acid sequence can facilitate conjugating or otherwise attaching the ASC-targeting peptide to a VLP.

The virus-like particle (VLP) can include any particle that includes viral protein assembled to structurally resemble the virus from which they are derived, but lack enough of the viral genome so that they are non-replicative and, therefore, noninfectious. A VLP may, therefore, include at least some of the viral genome, but the viral genome is genetically modified so that the viral genes responsible for infectivity and/or replication are inactivated. Exemplary VLPs include, but are not limited to, VLPs of Qβ, MS2, PP7, AP205, and other bacteriophage coat proteins, the capsid and core proteins of Hepatitis B virus, measles virus, Sindbis virus, rotavirus, foot-and-mouth-disease virus, Norwalk virus, the retroviral GAG protein, the retrotransposon Ty protein pl, the surface protein of Hepatitis B virus, human papilloma virus, human polyoma virus, RNA phages, Ty, frphage, GA-phage, AP 205-phage and, in particular, Qβ-phage, Cowpea chlorotic mottle virus, cowpea mosaic virus, human papilloma viruses (HPV), bovine papilloma viruses, porcine parvovirus, parvoviruses such as B19, porcine (PPV) and canine (CPV) parvovirues, caliciviruses (e.g. Norwalk virus, rabbit hemorrhagic disease virus [RHDV]), animal hepadnavirus core Antigen VLPs, filamentous/rod-shaped plant viruses, including but not limited to Tobacco Mosaic Virus (TMV), Potato Virus X (PVX), Papaya Mosaic Virus (PapMV), Alfalfa Mosaic Virus (AIMV), and Johnson Grass Mosaic Virus (JGMV), insect viruses such as flock house virus (FHV) and tetraviruses, polyomaviruses such as Murine Polyomavirus (MPyV), Murine Pneumotropic Virus (MPtV), BK virus (BKV), and JC virus (JCV).

The antigenic ASC peptides may be coupled to immunogenic carriers via chemical conjugation or by expression of genetically engineered fusion partners. The coupling does not necessarily need to be direct, but can occur through linker sequences. More generally, in the case that antigenic peptides either fused, conjugated, or otherwise attached to an immunogenic carrier, spacer sequence, or linker sequence are typically added at one or both ends of the antigenic peptides. Such linker sequences generally comprise sequences recognized by the proteasome, proteases of the endosomes or other vesicular compartment of the cell.

In one embodiment, the antigenic ASC peptide may be displayed as fusion protein with a subunit of the immunogenic carrier. Fusion of the peptide can be effected by inserting the ASC antigenic peptide amino acid sequence into the immunogenic carrier primary sequence, or by fusion to either the N-terminus or C-terminus of the immunogenic carrier.

When the immunogenic carrier is a VLP, the chimeric antigenic peptide-VLP subunit can be capable of self-assembly into a VLP. VLP displaying epitopes fused to their subunits are also herein referred to as chimeric VLPs. For example, European Application No. EP90310264A (European Patent No. EP0421635 B1) describes the use of chimeric hepadnavirus core antigen particles to present foreign peptide sequences in a virus-like particle.

Flanking amino acid residues may be added to either end of the sequence of the antigenic ASC-targeting peptide to be fused to either end of the sequence of the subunit of a VLP, or for internal insertion of such peptide sequence into the sequence of the subunit of a VLP. Glycine and serine residues are particularly favored amino acids to be used in the flanking sequences added to the peptide to be fused. Glycine residues confer additional flexibility, which may diminish the potentially destabilizing effect of fusing a foreign sequence into the sequence of a VLP subunit.

In one or more embodiments, the immunogenic carrier is a VLP of a RNA phage such as, for example, Qβ. The major coat proteins of RNA phages spontaneously assemble into VLPs upon expression in bacteria such as, for example, E. coli. Fusion protein constructs wherein antigenic peptides have been fused to the C-terminus of a truncated form of the A1 protein of Qβ, or inserted within the A1 protein have been described (Kozlovska et al., 1996, Intervirology 39: 9-15). Assembly of Qβ particles displaying the fused epitopes typically involves the presence of both the Al protein-antigen fusion and the wild type coat protein to form a mosaic particle. However, embodiments involving VLPs, and in particular the VLPs of the RNA phage Qβ coat protein, that are exclusively composed of VLP subunits having an antigenic peptide fused thereto, are contemplated.

The production of mosaic particles may be effected in a number of ways. In one exemplary approach, efficient display of the fused epitope on the VLPs is mediated by the expression of the plasmid encoding the Qβ A1 protein fusion having a UGA stop codon between the coat protein and the coat protein extension in an E. coli strain harboring a plasmid encoding a cloned UGA suppressor tRNA, which leads to translation of the UGA codon into Trp (pISM3001 plasmid). In a second exemplary approach, the coat protein gene stop codon is modified into UAA, and a second plasmid expressing the A1 protein-antigen fusion is co-transformed. The second plasmid encodes a different antibiotic resistance and the origin of replication is compatible with the first plasmid. In a third exemplary approach, Qβ coat protein and the A1 protein-antigen fusion are encoded in a bicistronic manner, operatively linked to a promoter such as the Trp promoter.

Further VLPs suitable for fusion of antigens or antigenic determinants are described in, for example, International Patent Application No. PCT/IB2002/004132 (International Publication No. WO 03/024481 A2) and include bacteriophage fr, RNA phase MS-2, capsid protein of papillomavirus, retrotransposon Ty, yeast and also Retrovirus-like-particles, HIV2 Gag, Cowpea Mosaic Virus, parvovirus VP2 VLP, HBsAg (U.S. Pat. No. 4,722,840). Examples of chimeric VLPs suitable for use as the immunogenic carrier include those described in Kozlovska et al., 1996, Intervirology 39:9-15. Further examples of VLPs suitable for use as the immunogenic carrier include, but are not limited to, HPV-1, HPV-6, HPV-11, HPV-16, HPV-18, HPV-33, HPV-45, CRPV, COPV, HIV GAG, Tobacco Mosaic Virus, Virus-like particles of SV-40, Polyomavirus, Adenovirus, Herpes Simplex Virus, Rotavirus, and Norwalk virus.

In one or more embodiments, a vaccine construct containing the ASC peptide containing the amino acid sequence of SEQ ID NO3, SEQ ID NO:4, or SEQ ID NO:5 is synthesized by conjugating the peptide to Qβ bacteriophage VLPs using a bifunctional cross-linker (SMPH). The ASC peptide can be modified to include a linker peptide to the C-terminus (e.g., a GGGC linker sequence; SEQ ID NO:6)

or the N-terminus (e.g., a CGGG linker sequence; SEQ ID NO:7) to the N-terminus. The SMPH cross-linker conjugates free amines on the surface of the Qβ VLPs to the cysteine residue of the linker peptide. In one exemplary synthesis methodology, the Qβ VLP is purified from free, unconjugated crosslinker, and then reacted with the ASC peptide at a molar ratio of about 10 peptide: 1 VLP.

For any recombinantly expressed antigenic ASC peptide described herein (whether or not coupled to an immunogenic carrier), this disclosure describes an isolated nucleic acid sequence that encodes any embodiment of an antigenic ASC-targeting peptide, or any component fragment of an antigenic ASC-targeting peptide, having the amino acid sequence of any one of SEQ ID NO:1, SEQ ID NO:2, or any fragment thereof. In some embodiments, the isolated nucleic acid encodes an antigenic ASC-targeting peptide that includes the amino acids of SEQ ID NO:3, SEQ ID NO:4, or SEQ ID NO:5. Given the amino acid sequence of any antigenic ASC-targeting peptide, or one or more component fragments of the antigenic ASC-targeting peptide, a person of ordinary skill in the art can determine the full scope of polynucleotides that encode that amino acid sequence using conventional, routine methods.

As used herein, the term "nucleic acid" or "oligonucleotide" refers to polynucleotides such as deoxyribonucleic acid (DNA) or ribonucleic acid (RNA). Nucleic acids include but are not limited to genomic DNA, cDNA, mRNA, iRNA, miRNA, tRNA, ncRNA, rRNA, and recombinantly produced and chemically synthesized molecules such as aptamers, plasmids, anti-sense DNA strands, shRNA, ribozymes, nucleic acids conjugates, and oligonucleotides. A nucleic acid may be single-stranded, double-stranded, linear, or covalently circularly closed molecule. A nucleic acid can be isolated. The term "isolated nucleic acid" means that the nucleic acid (i) was amplified in vitro, for example via polymerase chain reaction (PCR), (ii) was produced recombinantly by cloning, (iii) was purified, for example, by cleavage and separation by gel electrophoresis, (iv) was synthesized, for example, by chemical synthesis, or (vi) extracted from a sample. A nucleic might be introduced—i.e., transfected—into cells. When RNA is used to transfect cells, the RNA may be modified by stabilizing modifications, capping, or polyadenylation.

As used herein "amplified DNA" or "PCR product" refers to an amplified fragment of DNA of defined size. Various techniques are available and well known in the art to detect PCR products. PCR product detection methods include, but are not restricted to, gel electrophoresis using agarose or polyacrylamide gel and adding ethidium bromide staining (a DNA intercalant), labeled probes (radioactive or non-radioactive labels, southern blotting), labeled deoxyribonucleotides (for the direct incorporation of radioactive or non-radioactive labels) or silver staining for the direct visualization of the amplified PCR products; restriction endonuclease digestion, which relies on agarose gel electrophoresis, polyacrylamide gel electrophoresis, or high-performance liquid chromatography (HPLC); dot blots, using the hybridization of the amplified DNA on specific labeled probes (radioactive or non-radioactive labels); high-pressure liquid chromatography using ultraviolet detection; electro-chemiluminescence coupled with voltage-initiated chemical reaction/photon detection; and direct sequencing using radioactive or fluorescently labeled deoxyribonucleotides for the determination of the precise order of nucleotides with a DNA fragment of interest, oligo ligation assay (OLA), PCR, qPCR, DNA sequencing, fluorescence, gel electrophoresis, magnetic beads, allele specific primer extension (ASPE) and/or direct hybridization.

Generally, nucleic acid can be extracted, isolated, amplified, or analyzed by a variety of techniques such as those described by Green and Sambrook, Molecular Cloning: A Laboratory Manual (Fourth Edition), Cold Spring Harbor Laboratory Press, Woodbury, NY 2,028 pages (2012); or as described in U.S. Pat. Nos. 7,957,913; 7,776,616; 5,234,809; and 9,012,208. Examples of nucleic acid analysis include, but are not limited to, sequencing and DNA-protein interaction. Sequencing may be by any method known in the art. DNA sequencing techniques include classic dideoxy sequencing reactions (Sanger method) using labeled terminators or primers and gel separation in slab or capillary, and next generation sequencing methods such as sequencing by synthesis using reversibly terminated labeled nucleotides, pyrosequencing, 454 sequencing, Illumina/Solexa sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing. Separated molecules may be sequenced by sequential or single extension reactions using polymerases or ligases as well as by single or sequential differential hybridizations with libraries of probes.

In another aspect, this disclosure describes a host cell including any of the isolated nucleic acid sequences and/or proteins described herein. Thus, this disclosure encompasses translation of a nucleic acid (e.g., an mRNA) by a host cell to produce an ASC-VLP subunit.

The nucleic acid constructs of the present invention may be introduced into a host cell to be altered, thus allowing expression of the ASC-VLP subunit peptide within the cell, thereby generating a genetically engineered cell. A variety of methods are known in the art and suitable for introducing a nucleic acid into a cell, including viral and non-viral mediated techniques. Examples of typical non-viral mediated techniques include, but are not limited to, electroporation, calcium phosphate mediated transfer, nucleofection, sonoporation, heat shock, magnetofection, liposome mediated transfer, microinjection, microprojectile mediated transfer (nanoparticles), cationic polymer mediated transfer (DEAE-dextran, polyethylenimine, polyethylene glycol (PEG) and the like) or cell fusion. Other methods of transfection include proprietary transfection reagents such as LIPOFECTAMINE (Thermo Fisher Scientific, Inc., Waltham, MA), HILYMAX (Dojindo Molecular Technologies, Inc., Rockville, MD), FUGENE (Promega Corp., Madison, WI), JETPEI (Polyplus Transfection, Illkirch, France), EFFECTENE (Qiagen, Hilden, Germany) and DreamFect (OZ Biosciences, Inc USA, San Diego, CA).

The nucleic acid constructs described herein may be introduced into a host cell to be altered, thus allowing expression within the cell of the protein encoded by the nucleic acid. A variety of host cells are known in the art and suitable for protein expression. Examples of typical cell used for transfection and protein expression include, but are not limited to, a bacterial cell, a eukaryotic cell, a yeast cell, an insect cell, or a plant cell such as, for example, *E. coli, Bacillus, Streptomyces, Pichia pastoris, Salmonella typhimurium, Drosophila* S2, *Spodoptera* SJ9, CHO, COS (e.g., COS-7), 3T3-F442A, HeLa, HUVEC, HUAEC, NIH 3T3, Jurkat, 293, 293H, or 293F.

In one or more embodiments, the antigenic ASC peptide can be chemically coupled to the immunogenic carrier using techniques well known in the art. Conjugation can occur to allow free movement of peptides via single point conjugation (e.g., either N-terminal or C-terminal point) or as a locked down structure where both ends of peptides are conjugated to either an immunogenic carrier protein or to a scaffold structure such as a VLP. Conjugation occurs via conjugation chemistry known to those skilled in the art such as via cysteine residues, lysine residues, or another carboxy moiety. Thus, for example, for direct covalent coupling, it is possible to use a carbodiimide, glutaraldehyde, or N-[γ-maleimidobutyryloxy] succinimide ester, using common commercially available hetero-bifunctional linkers such as 1-cyano-4-dimethylaminopyridinium tetrafluoroborate (CDAP) or succinimidyl 3-(2-pyridyldithio)propionate (SPDP).

Examples of conjugation of peptides, particularly cyclized peptides, to a protein carrier via acylhydrazine peptide derivatives are described in, for example, International Patent Application No. PCT/EP2003/004551 (International Publication No. WO 2003/092714 A1). After the coupling reaction, the immunogen can easily be isolated and purified using, for example, a dialysis method, a high performance liquid chromatography method, a gel filtration method, a fractionation method, etc. Peptides terminating with a cysteine residue (preferably with a linker outside the cyclized region) may be conveniently conjugated to a carrier protein via maleimide chemistry.

When the immunogenic carrier is a VLP, several antigenic peptides, either having an identical amino acid sequence or a different amino acid sequence, may be coupled to a single VLP particle, leading preferably to a repetitive and ordered structure presenting several antigenic determinants in an oriented manner as described in International Patent Applications PCT/IB1999/001925 (International Publication No. WO 00/032227), PCT/IB2002/004132 (International Publication No. WO 2003/024481), PCT/IB2002/000166 (International Publication No. WO 02/056905), and PCT/EP2003/007572 (International Publication No. WO 2004/007538). Thus, the antigenic peptide displayed by one VLP subunit in a VLP may the same or different than the antigenic peptide displayed by a second VLP subunit in the same VLP. In other embodiments, one or several antigen molecules can be attached to one VLP subunit. A specific feature of the VLP of the coat protein of RNA phages, and in particular of the Qβ coat protein VLP, is thus the possibility to couple several antigens per subunit. This allows for the generation of a dense antigen array.

Another feature of VLPs derived from RNA phage is their high expression yield in bacteria that allows production of large quantities of material at affordable cost. Moreover, the use of the VLPs as carriers allows the formation of robust antigen arrays and conjugates, respectively, with variable antigen density. In particular, the use of VLPs of RNA phages, and in particular the use of the VLP of RNA phage Qβ coat protein, allows a very high antigen density to be achieved.

The ASC-targeting VLP may be used to treat a subject having, or at risk of having, an inflammatory condition involving, at least in part, by inflammasome assembly and/or inflammatory cytokines.

As used herein, "treat" or variations thereof refer to reducing, limiting progression, ameliorating, or resolving, to any extent, the symptoms or signs related to a condition. A "sign" or "clinical sign" refers to an objective physical finding relating to a particular condition capable of being found by one other than the subject. A "symptom" refers to any subjective evidence of disease or of a subject's condition.

A "treatment" may be therapeutic or prophylactic. "Therapeutic" and variations thereof refer to a treatment that ameliorates one or more existing symptoms or clinical signs associated with a condition. "Prophylactic" and variations thereof refer to a treatment that limits, to any extent, the development and/or appearance of a symptom or clinical sign of a condition. Generally, a "therapeutic" treatment is initiated after the condition manifests in a subject, while "prophylactic" treatment is initiated before a condition manifests in a subject.

Treatment that is prophylactic—e.g., initiated before a subject manifests a symptom or clinical sign of the condition such as, for example, while an inflammatory condition remains subclinical—is referred to herein as treatment of a subject that is "at risk" of having the condition. As used herein, the term "at risk" refers to a subject that may or may not actually possess the described risk. Thus, for example, a subject "at risk" of developing a condition is a subject possessing one or more risk factors associated with the condition such as, for example, genetic predisposition, ancestry, age, sex, geographical location, lifestyle, or medical history. Thus, the ASC-targeted VLP may be administered prophylactically before a subject manifests a symptom or clinical sign of an inflammatory condition.

Accordingly, a composition can be administered before, during, or after the subject first exhibits a symptom or clinical sign of an inflammatory condition. Treatment initiated before the subject first exhibits a symptom or clinical sign associated with the inflammatory condition may result in decreasing the likelihood that the subject experiences clinical evidence of the inflammatory condition compared to a subject to which the composition is not administered, decreasing the severity of symptoms and/or clinical signs of the condition, and/or completely resolving the inflammatory condition. Treatment initiated after the subject first exhibits a symptom or clinical sign associated with the inflammatory condition may result in decreasing the severity of symptoms and/or clinical signs of the inflammatory condition compared to a subject to which the composition is not administered, and/or completely resolving the inflammatory condition.

Thus, the method includes administering an effective amount of the composition to a subject having, or at risk of having, an inflammatory condition involving inflammasome assembly and/or inflammatory cytokines. In this aspect, an "effective amount" is an amount effective to reduce, limit progression, ameliorate, or resolve, to any extent, a symptom or clinical sign related to the inflammatory condition.

Thus, the ASC-targeting Qβ VLP described herein may be formulated with a pharmaceutically acceptable carrier. As used herein, "carrier" includes any solvent, dispersion medium, vehicle, coating, diluent, antibacterial, and/or antifungal agent, isotonic agent, absorption delaying agent, buffer, carrier solution, suspension, colloid, and the like. The use of such media and/or agents for pharmaceutical active substances is well known in the art. Except insofar as any conventional media or agent is incompatible with the active ingredient, its use in the therapeutic compositions is contemplated. Supplementary active ingredients also can be incorporated into the compositions. As used herein, "pharmaceutically acceptable" refers to a material that is not biologically or otherwise undesirable, i.e., the material may be administered to an individual along with the ASC-targeting Qβ VLP without causing any undesirable biological effects or interacting in a deleterious manner with any of the other components of the pharmaceutical composition in which it is contained.

The ASC-targeting Qβ VLP may therefore be formulated into a pharmaceutical composition. The pharmaceutical composition may be formulated in a variety of forms adapted to a preferred route of administration. Thus, a composition can be administered via known routes including, for example, oral, parenteral (e.g., intradermal, transcutaneous, subcutaneous, intramuscular, intravenous, intraperitoneal, etc.), or topical (e.g., intranasal, intrapulmonary, intramammary, intravaginal, intrauterine, rectally, etc.). A pharmaceutical composition can be administered to a mucosal surface, such as by administration to, for example, the nasal or respiratory mucosa (e.g., by spray or aerosol). A composition also can be administered via a sustained or delayed release.

Thus, an ASC-targeting Qβ VLP may be provided in any suitable form including but not limited to a solution, a suspension, an emulsion, a spray, an aerosol, or any form of mixture. The composition may be delivered in formulation with any pharmaceutically acceptable excipient, carrier, or vehicle. For example, the formulation may be delivered in a conventional topical dosage form such as, for example, a cream, an ointment, an aerosol formulation, a non-aerosol spray, a gel, a lotion, and the like. The formulation may further include one or more additives including such as, for example, an adjuvant (whether an ADVAX adjuvant or other adjuvant), a skin penetration enhancer, a colorant, a fragrance, a flavoring, a moisturizer, a thickener, and the like.

A formulation may be conveniently presented in unit dosage form and may be prepared by methods well known in the art of pharmacy. Methods of preparing a composition with a pharmaceutically acceptable carrier include the step of bringing the ASC-targeting Qβ VLP into association with a carrier that constitutes one or more accessory ingredients. In general, a formulation may be prepared by uniformly and/or intimately bringing the active compound into association with a liquid carrier, a finely divided solid carrier, or both, and then, if necessary, shaping the product into the desired formulations.

The amount of ASC-targeting Qβ VLP administered can vary depending on various factors including, but not limited to, the inflammatory condition being treated, the weight, physical condition, and/or age of the subject, and/or the route of administration. Thus, the absolute weight of ASC-targeting Qβ VLP included in a given unit dosage form can vary widely, and depends upon factors such as the species, age, weight, and physical condition of the subject, and/or the method of administration. Accordingly, it is not practical to set forth generally the amount that constitutes an amount of ASC-targeting Qβ VLP effective for all possible applications. Those of ordinary skill in the art, however, can readily determine the appropriate amount with due consideration of such factors.

In one or more embodiments, the method can include administering sufficient ASC-targeting Qβ VLP to provide a dose of, for example, from about 50 ng/kg to about 1 mg/kg to the subject, although in one or more embodiments the methods may be performed by administering ASC-targeting Qβ VLP in a dose outside this range.

Dosing

In one or more embodiments, the method includes administering sufficient ASC-targeting Qβ VLP to provide a minimum dose of at least 50 ng/kg such as, for example, at least 100 ng/kg, at least 200 ng/kg, at least 300 ng/kg, at least 400 ng/kg, at least 500 ng/kg, at least 600 ng/kg, at least 700 ng/kg, at least 800 ng/kg, at least 900 ng/kg, at least 1 µg/kg, at least 2 µg/kg, at least 5 µg/kg, at least 10 µg/kg, at least 20 µg/kg, at least 50 µg/kg, at least 100 µg/kg, at least 200 µg/kg, or at least 500 µg/kg.

In one or more embodiments, the method includes administering sufficient ASC-targeting Qβ VLP to provide a maximum dose of no more than 1 mg/kg, no more than 500 µg/kg, no more than 250 µg/kg, no more than 200 µg/kg, no more than 150 µg/kg, no more than 100 µg/kg, no more than 50 µg/kg, no more than 25 µg/kg, no more than 10 µg/kg, no more than 5 µg/kg, no more than 2 µg/kg, no more than 1 µg/kg, no more than 800 ng/kg, no more than 600 ng/kg, no more than 500 ng/kg, no more than 400 ng/kg, no more than 300 ng/kg, no more than 250 ng/kg, no more than 150 ng/kg, no more than 100 ng/kg, no more than 50 ng/kg, or no more than 25 ng/kg.

In one or more embodiments, the method includes administering sufficient ASC-targeting Qβ VLP to provide a dose that falls within a range having as endpoints any minimum dose listed above and any maximum dose listed above that is greater than the minimum does. For example, in one or more embodiments, the method can includes administering sufficient ASC-targeting Qβ VLP to provide a dose of from 200 ng/kg to about 10 µg/kg to the subject, for example, a dose of from about 700 ng/kg to about 5 µg/kg.

In one or more embodiments, ASC-targeting Qβ VLP may be administered, for example, from a single dose to multiple doses per week, although in one or more embodiments the method can be performed by administering ASC-targeting Qβ VLP at a frequency outside this range. When multiple doses are used within a certain period, the amount of each dose may be the same or different. For example, a dose of 1 mg per day may be administered as a single dose of 1 mg, two 0.5 mg doses, or as a first dose of 0.75 mg followed by a second dose of 0.25 mg. Also, when multiple doses are used within a certain period, the interval between doses may be the same or be different.

Dosing Frequency

In certain embodiments, ASC-targeting Qβ VLP may be administered at minimum frequency of at least once per year such as, for example, at least once every six months, at least once every four months, at least once every three months, at least once every two months, at least once per month, or at least once every two weeks.

In certain embodiments, ASC-targeting Qβ VLP may be administered at maximum frequency of no more than once per week such as, for example, no more than once every two weeks, no more than once per month, no more than once every two months, no more than once every three months, no more than once every six months, or once per year.

In one or more embodiments, ASC-targeting Qβ VLP may be administered at a frequency defined by a range having as endpoints any minimum frequency listed above and any maximum frequency listed above that is more frequent than the minimum frequency.

Duration of Treatment

The duration of administration of an antigenic ASC peptide described herein, e.g., the period of time over which an antigenic ASC peptide is administered, can vary, depending on any of a variety of factors, e.g., patient response, etc. For example, an antigenic ASC peptide can be administered over a period of time ranging from about one day to about one week, from about two weeks to about four weeks, from about one month to about two months, from about two months to about four months, from about four months to about six months, from about six months to about eight months, from about eight months to about one year, from about one year to about two years, or from about two years to about four years, or more. In one or more embodiments, the ASC-targeting Qβ VLP may be administered as a once off treatment. In other embodiments, the ASC-targeting Qβ VLP may be administered for the life of the subject. In certain embodiments, the ASC-targeting Qβ VLP may be administered monthly (e.g., every four weeks) until effective.

In some cases, the ASC-targeting Qβ VLP may be administered at an initial frequency for an initial period and then administered at a lower frequency thereafter. For example, a dosing regimen may include administering three doses of the ASC-targeting Qβ VLP at a frequency of once per month (i.e., an initial dose followed by a second dose one month after the initial dose) followed by an additional dose six months after the initial dose.

When an ASC-targeting Qβ VLP composition is used for prophylactic treatment, it may be generally administered for priming and/or boosting doses. Boosting doses, when administered, are adequately spaced (e.g., yearly) to boost the level of circulating antibody that has fallen below a desired level. Boosting doses may include an ASC-targeting peptide either with or in the absence of the original immunogenic carrier. A booster composition may include an alternative immunogenic carrier or may be in the absence of any carrier. Moreover, a booster composition may be formulated either with or without adjuvant.

In one exemplary embodiment, the ASC-VLP vaccine may be administered in a three-dose regimen, with the three doses administered at an interval of one and six months or a range between one and twelve months. Additional boosters may be administered as needed at an appropriate frequency (e.g., every twelve months). In one exemplary embodiment, the treatment regimen can include a first dose of 100 µg of VLP or a range of 50 µg to 300 µg of VLP and repeated booster doses of from 50 µg to 300 µg of VLP (e.g., 100 µg of VLP).

In one or more embodiments, the ASC-VLP vaccine can be combined with one or more additional therapeutic agents. The one or more additional therapeutic agents may be administered before, after, and/or coincident to the administration of the ASC-VLP vaccine. An ASC-VLP vaccine and the additional therapeutic agents may be co-administered. As used herein, "co-administered" refers to two or more components of a combination administered so that the therapeutic or prophylactic effects of the combination can be greater than the therapeutic or prophylactic effects of either component administered alone. Two components may be co-administered simultaneously or sequentially. Simultaneously co-administered components may be provided in one or more pharmaceutical compositions. Sequential co-administration of two or more components includes cases in which the components are administered so that each component can be present at the treatment site at the same time. Alternatively, sequential co-administration of two components can include cases in which at least one component has been cleared from a treatment site, but at least one cellular effect of administering the component (e.g., inactivation of the inflammasome, inhibition of one or more inflammatory cytokines, etc.) persists at the treatment site until one or more additional components are administered to the treatment site. Thus, a co-administered combination can, in certain circumstances, include components that never exist in a chemical mixture with one another. In one or more alternative embodiments, the ASC-VLP vaccine and the additional therapeutic agent may be administered as part of a mixture or cocktail. In some aspects, the administration of an ASC-VLP vaccine may allow for the effectiveness of a lower dosage of other therapeutic modalities when compared to the administration of the other therapeutic agent or agents alone, thereby decreasing the likelihood, severity, and/or extent of the toxicity observed when a higher dose of the other therapeutic agent or agents is administered.

Exemplary additional therapeutic agents include, but are not limited to, anti-ASC antibody preparations. Exemplary anti-ASC antibody preparations include, but are not limited to, an antibody directed to full-length ASC (e.g., mAb, 04-147, clone 2EI-7, 1:1,000 dilution, MilliporeSigma, Burlington, MA), an antibody directed to the CARD region (e.g., mAb, 653902, clone TMS-1, 1:500 dilution, BioLegend, San Diego, CA; pAb, sc-22514-R, clone N-15R, 1:200 dilution, Santa Cruz Biotechnology, Inc., Dallas, TX)

In the preceding description and following claims, the term "and/or" means one or all of the listed elements or a combination of any two or more of the listed elements; the terms "comprises," "comprising," and variations thereof are to be construed as open ended—i.e., additional elements or steps are optional and may or may not be present; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Reference throughout this specification to "one embodiment," "an embodiment," "certain embodiments," "some embodiments," or "one or more embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments. Furthermore, the particular features, configurations, compositions, or characteristics may be combined in any suitable manner in one or more embodiments. Thus, features described in the context of one embodiment may be combined with features described in the context of a different embodiment except where the features are necessarily mutually exclusive.

For any method disclosed herein that includes discrete steps, the steps may be conducted in any feasible order. And, as appropriate, any combination of two or more steps may be conducted simultaneously.

As used herein, the terms "preferred" and "preferably" refer to embodiments of the invention that may afford certain benefits under certain circumstances. However, other embodiments may also be preferred under the same or other circumstances. Furthermore, the recitation of one or more preferred embodiments does not imply that other embodiments are not useful and is not intended to exclude other embodiments from the scope of the invention.

The present invention is illustrated by the following examples. It is to be understood that the particular examples, materials, amounts, and procedures are to be interpreted broadly in accordance with the scope and spirit of the invention as set forth herein.

EXAMPLES

Qβ-VLPs were produced in *Escherichia coli* (*E. coli*) using previously described methods (Crossey, E. et al. *Vaccine.* 2015). ASC peptides were synthesized (GenScript Biotech Corp., Piscataway, NJ) and stored as a lyophilized powder at −20° C. ASC peptides were conjugated to surface exposed lysines on assembled VLPs using the bi-functional crosslinker, succinimidyl 6-[(beta-maleimidopropionamido) hexanoate] (SMPH; Thermo Fisher Scientific, Inc., Waltham, MA) (FIG. 3). Efficiency of conjugation was confirmed via mobility shift gel electrophoresis on a 10% SDS denaturing polyacrylamide gel (FIG. 4).

C57Bl/6J mice were obtained from The Jackson Laboratory (Bar Harbor, ME) and aged to 2-months old. Mice were randomized according to sex and assigned to either Qβ Control Sham treatment, Qβ ASC-Linker, Qβ ASC-Helix4, or Qβ ASC-C-term vaccine treatment (n=5 per group). Vaccines were administered via intramuscular injection in the right hindlimb at a dose of 5 μg of VLP (10 μg for the ASC-C-term vaccine due to poor conjugation efficiency) suspended in 50 μL of sterile water (100-200 ng/μL concentration) at two months of age followed by a booster vaccine three weeks later. (FIG. 5).

Three weeks after the second injection, blood plasma samples were obtained via retro orbital capillary collection and antibody titers were assessed using indirect enzyme-linked immunosorbent assays (ELISA) against the target peptide used to synthesize the vaccine. Immune sera from the vaccinated mice was used as the primary antibody at multiple dilutions and was detected using a horseradish peroxidase-conjugated goat anti-mouse antibody with 3,3', 5,5'-tetramethylbenzidine (TMB) substrate with absorbance measured at 450 nm (FIGS. 6-8).

The vaccinated animals were observed weekly for any signs of deteriorating health including poor grooming behaviors, lethargy, dermatitis, masses, open wounds, or other evidence of infection. Animal weights were collected at four time points including at two months, three months, five months, and six months of age (FIG. 9). At six months of age, blood samples were obtained via retro orbital capillary collection into ethylene diamine tetra acetic acid (EDTA) and heparin coated tubes and then assessed using complete blood cell counts on the Abaxis Vetscan HM5 (FIG. 10) and mouse blood chemistry panel on the Abaxis Vetscan VS2 (FIG. 10).

Figure 14:
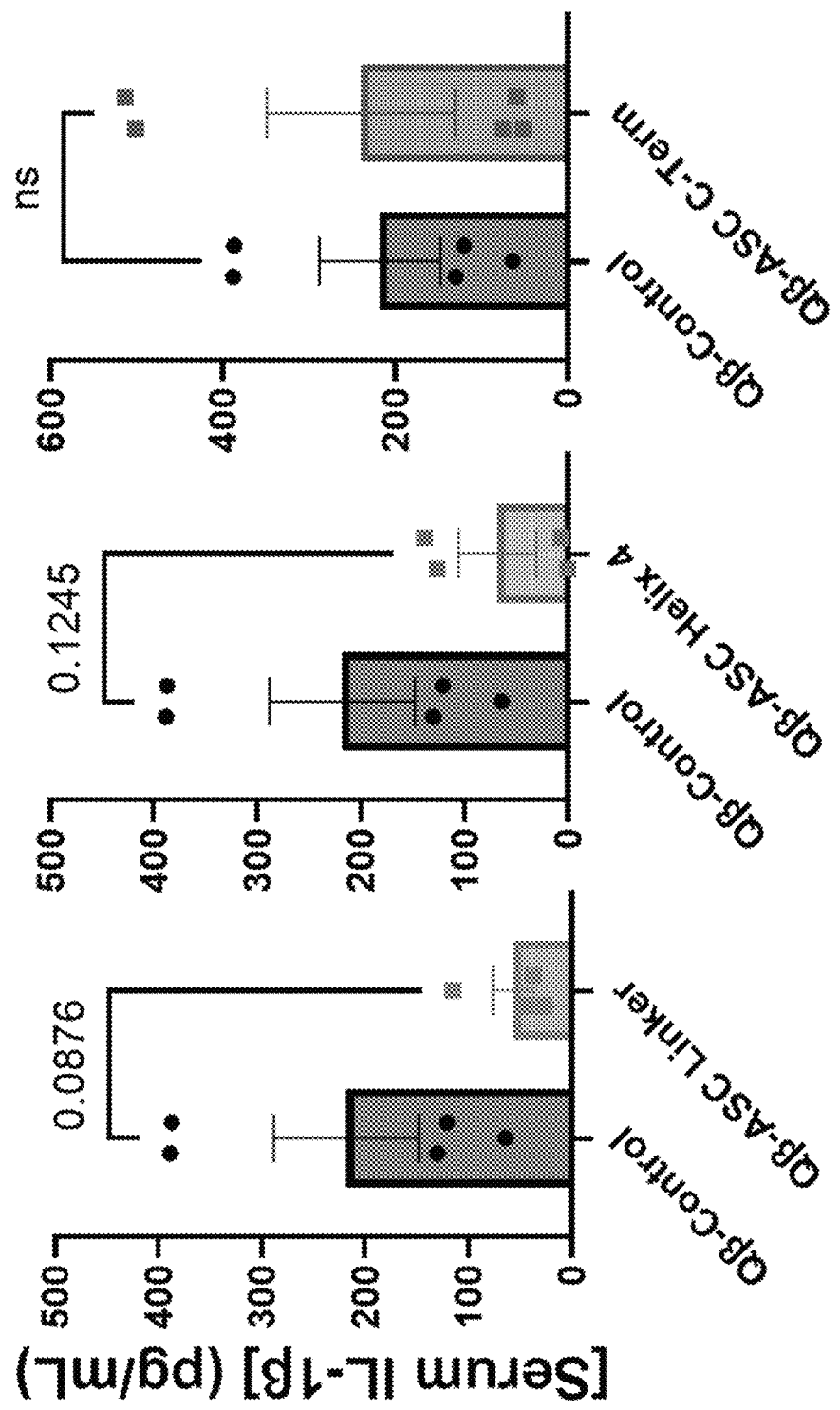
FIG. 14. ELISA-based quantification of serum interleukin-1β (IL-1B) levels in Qβ Control and Qβ-ASC VLP vaccinated mice injected with lipopolysaccharide (LPS) to induce an inflammasome response. Despite the low affinity of ASC VLP-elicited antibodies for mouse ASC protein, there was a trend towards decreased levels of mature IL-1β in the serum of Qβ-ASC Linker and Qβ-ASC Helix 4 vaccinated mice suggesting possible neutralization of endogenous mouse ASC protein in the serum by circulating Qβ-ASC VLP-elicited antibodies.

The vaccinated animals were then intraperitoneally injected with 5 mg/kg lipopolysaccharide (LPS; from *E. coli* 055: B5, MilliporeSigma, Burlington, MA) and sacrificed nine hours post-injection. Terminal blood collection by heart puncture was performed. Animals were then transcardially perfused with ice-cold 0.125 M phosphate buffer and brains were micro-dissected and frozen on dry ice. Blood samples were allowed to clot on ice for 30 minutes and then centrifuged twice at 5000 RPM for five minutes to isolate immune sera, which was stored at −80° C. Serum interleukin-1β levels were assessed using a mouse IL-1β DuoSet ELISA kit (R&D systems, Catalogue # DY401) according to manufacturer instructions with sera diluted 50% in reagent diluent (R&D Systems, Inc., Minneapolis, MN) (FIG. 14).

Figure 15:
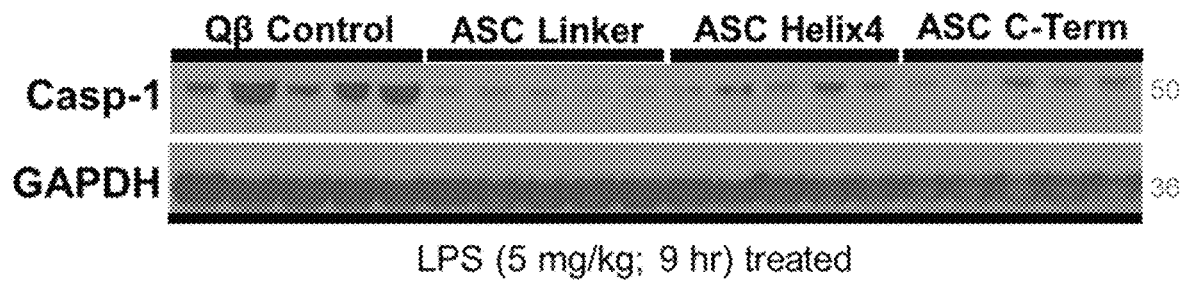
FIG. 15. Western blot of hippocampal brain lysates from Qβ Control and Qβ-ASC VLP vaccinated mice after stimulation with lipopolysaccharide (LPS) to induce inflammasome activation. Caspase-1, the downstream effector protein of the inflammasome, is significantly reduced in all Qβ-ASC VLP treated groups compared to the Qβ-Control group. p<0.01, *p<0.005. One-way ANOVA.
Figure 15:
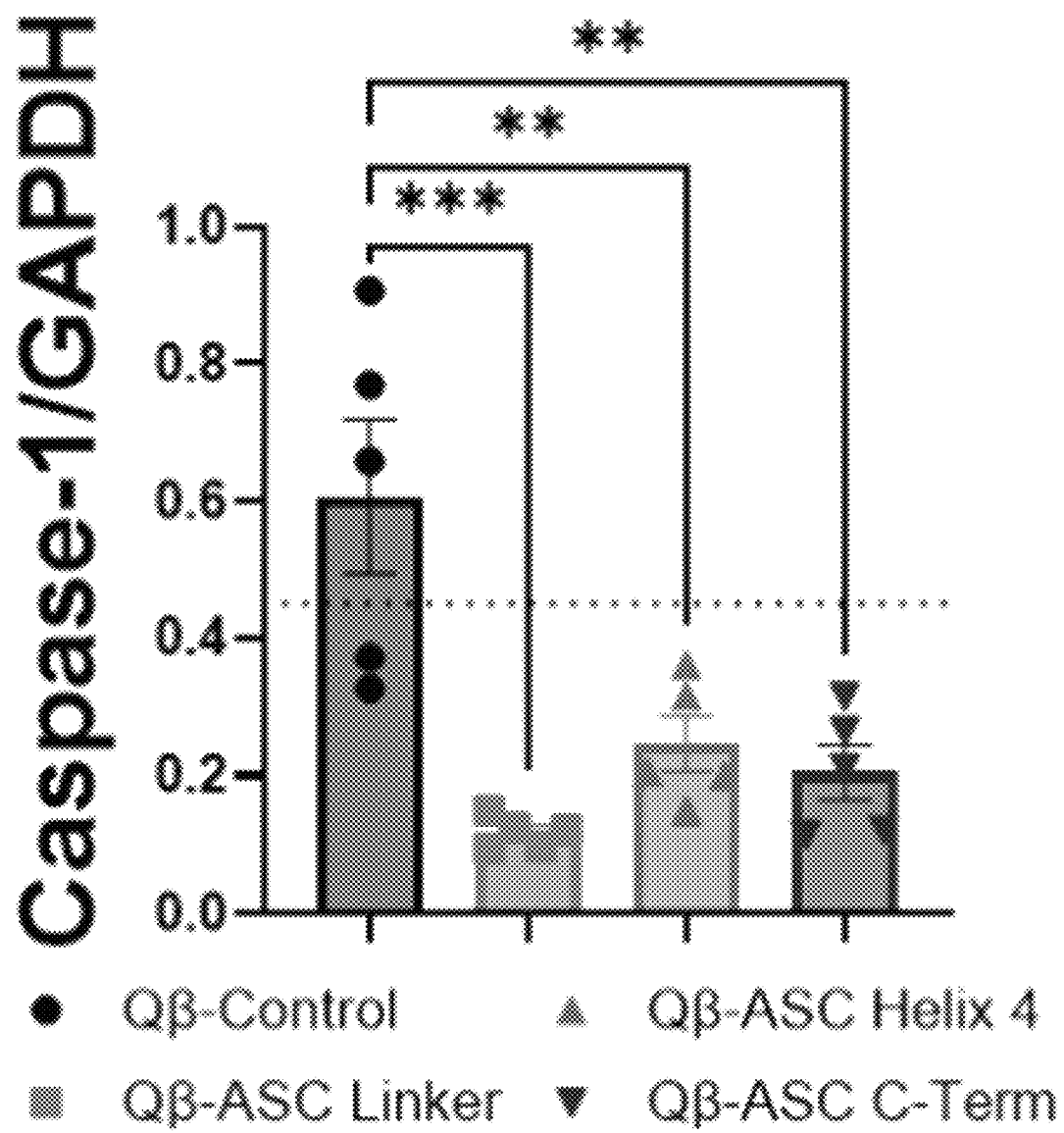

Hippocampal brain tissue samples were homogenized in 10% weight/volume Tissue Protein Extraction Reagent (T-PER, Thermo Fisher Scientific, Inc., Waltham, MA) with 1% protease inhibitor and phosphatase inhibitor (Thermo Fisher Scientific, Inc., Waltham, MA). Cells were lysed in 1×LDS/RA buffer (Thermo Fisher Scientific) and sonicated for 30 seconds, boiled at 95° C. for 15 minutes. Lysates were resolved via SDS-PAGE on a 4-12% Bis-Tris gradient gel and immunoblotted using caspase-1 p20 (AdipoGen Life Sciences, Inc., San Diego, CA) and GAPDH (MilliporeSigma, Burlington, MA) (FIG. 15).

Figure 11:
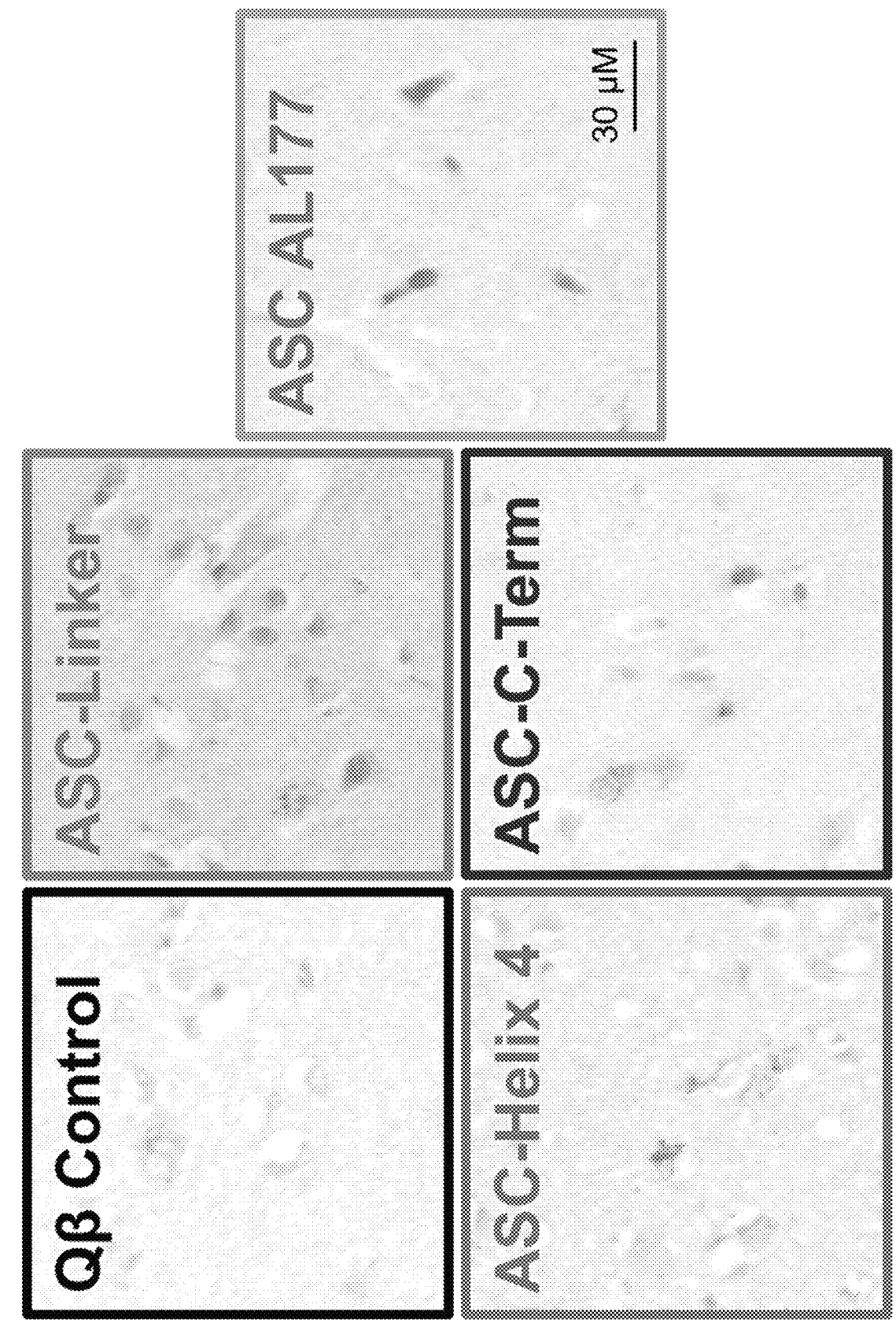
FIG. 11. Immunohistochemical micrographs of human hippocampal brain tissue from an Alzheimer's disease patient stained with an anti-ASC antibody (AdipoGen AL177) or immune sera from Qβ-Control or Qβ-ASC VLP vaccinated animals at a 1:500 dilution. Qβ-ASC VLP elicited antibodies bind to human ASC protein in human Alzheimer's disease brain tissue with strong staining in a similar pattern to commercially available anti-ASC antibodies. Qβ-Control immune sera only exhibit a low-level, non-specific background staining.

Formalin fixed and paraffin embedded human Alzheimer's disease hippocampal brain sections (n=1) were used for immunohistochemical analysis of ASC-VLP immune sera immunoreactivity. Sections were first sequentially hydrated in xylenes, ethanol, and PBS with 0.1% Tween (PBST) then incubated in 10 mM sodium citrate buffer (pH 6.0) for 30 minutes at 95° C. for antigen retrieval, washed in PBS with 0.1% Tween (PBST), quenched with 0.3% $H_2O_2$ in PBST for 20 minutes. Sections were blocked for one hour at room temperature with the 5% normal goat sera. The sections were incubated with rabbit polyclonal anti-ASC antibody (1:500, AdipoGen Life Sciences, Inc., San Diego, CA) or immune sera from Qβ Control or Qβ-ASC VLP vaccinated animals (1:500). After washing in PBST, the sections were incubated with biotinylated-secondary antibody (1:250, Jackson ImmunoResearch Laboratories Inc., West Grove, PA). Sections were then incubated with ABC (Vector Laboratories, Inc., Newark, CA) reagent for 30 minutes at room temperature. The immunoreactive signals were revealed by developing sections in SIGMAFAST 3,3'-diaminobenzidine (DAB) tablets (MilliporeSigma, Burlington, MA). The slides were dehydrated in ethanol and xylenes and then coverslipped and imaged using a brightfield microscope (FIG. 11).

Figure 12:
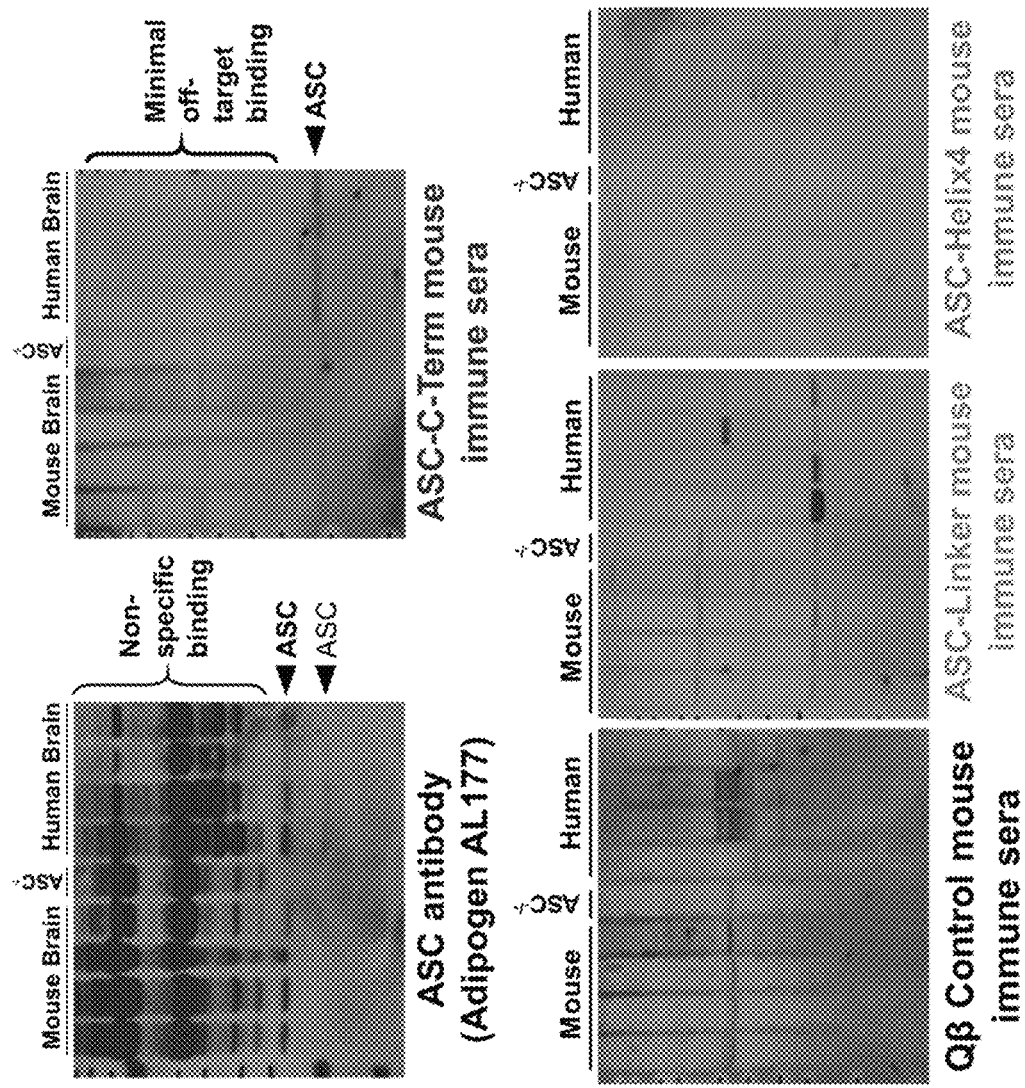
FIG. 12. Western blot of mouse and human hippocampal lysates stained with an anti-ASC antibody (AdipoGen AL177, 1:2000 dilution) or immune sera from Qβ-Control or Qβ-ASC VLP vaccinated animals (1:1000 dilution). Qβ-ASC VLP vaccination elicits a highly specific antibody response with less off-target binding than a commercially available antibody. Qβ-ASC Helix4 vaccine elicited antibodies did not show any binding to denatured protein, suggesting antibodies may be specific to the native protein conformation. Qβ-Control vaccinated immune sera showed substantial non-specific antibody binding at molecular weights overlapping with non-specific binding of the commercially available AL177 antibody. ASC-VLP elicited antibodies appear to preferentially bind to human protein over mouse protein.
Figure 13:
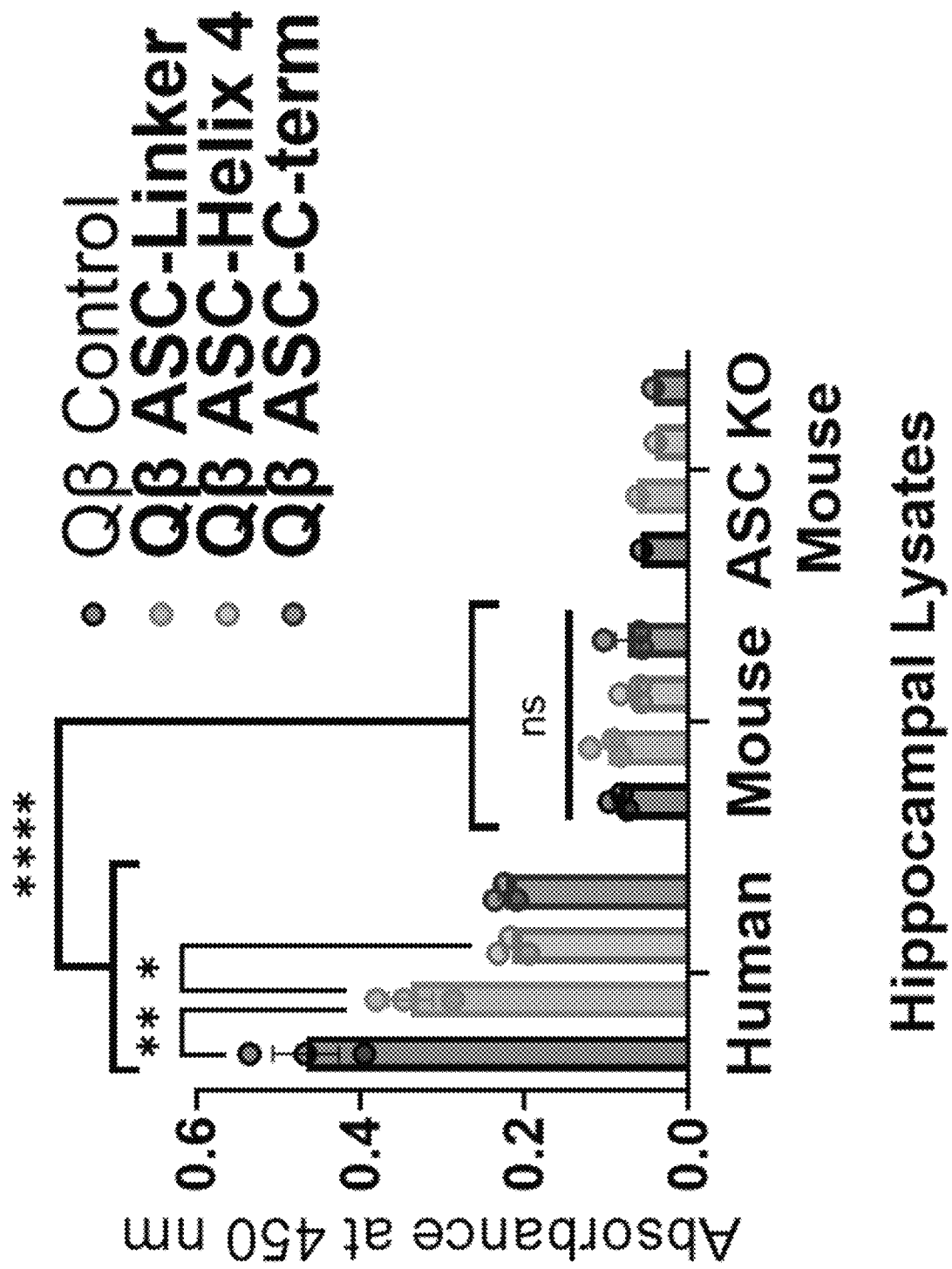
FIG. 13. Indirect sandwich ELISA of human and mouse hippocampal lysates using an anti-ASC antibody (AdipoGen AL177, 1:100 dilution) as the capture antibody and Qβ-Control or Qβ-ASC VLP immune sera (1:1000 dilution) as the detection antibody. An HRP-conjugated goat-anti-mouse antibody was used to detect the presence of bound vaccine-elicited antibodies using 3,3',5,5'-tetramethylbenzidine chromogenic substrate detected at 450 nm. Qβ-ASC VLP elicited antibodies preferentially bind human ASC protein over mouse ASC protein indicating a highly specific antibody response with limited protein cross-reactivity. High detection of Qβ-Control antibodies is likely due to overlap of non-specific protein binding with the AdipoGen AL177 antibody used as the protein capture antibody (see FIG. 12). **p<0.001, p<0.01, *p<0.05. One-way ANOVA.

Hippocampal brain lysates from non-vaccinated C57Bl6/J mice (n=4) injected with 5 mg/kg LPS and sacrificed nine hours later (as described above), $ASC^{-/-}$ transgenic mice (n=1), and human Alzheimer's disease patients (n=4) were used for assessing immune sera antibody cross-reactivity between human and mouse ASC. Hippocampal brain lysates were resolved via SDS-PAGE as described above and immunoblotted using rabbit polyclonal anti-ASC antibody (1:2000, AdipoGen Life Sciences, Inc., San Diego, CA) or immune sera from Qβ Control or Qβ-ASC VLP immune sera (1:1000) (FIG. 12). An indirect sandwich ELISA was performed using the rabbit polyclonal anti-ASC antibody (1:200, AdipoGen Life Sciences, Inc., San Diego, CA) as the capture antibody, incubating with hippocampal brain lysates from mice and humans for one hour at room temperature, and using Qβ Control or Qβ-ASC VLP immune sera as the detection antibody, followed by detection of bound anti-ASC antibodies using HRP-conjugated secondary antibody (1:10,000, Jackson ImmunoResearch Laboratories Inc., West Grove, PA) with TMB substrate absorbance at 450 nm (FIG. 13).

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

```
Sequence Listing Free Text
human ASC Sequence
                                              SEQ ID NO: 1
MGRARDAILD ALENLTAEEL KKFKLKLLSV PLREGYGRIP

RGALLSMDAL DLTDKLVSFY LETYGAELTA NVLRDMGLQE

MAGQLQAATH QGSGAAPAGI QAPPQSAAKP GLHFIDQHRA

ALIARVTNVE WLLDALYGKV LTDEQYQAVR AEPTNPSKMR

KLFSFTPAWN WTCKDLLLQA LRESQSYLVE DLERS
Pyrin domain: 1-91
CARD domain: 107-195 mouse ASC Sequence
                                              SEQ ID NO: 2
MGRARDAILD ALENLSGDEL KKFKMKLLTV QLREGYGRIP

RGALLQMDAI DLTDKLVSYY LESYGLELTM TVLRDMGLQE

LAEQLQTTKE ESGAVAAAAS VPAQSTARTG HFVDQHRQAL

IARVTEVDGV LDALHGSVLT EGQYQAVRAE TTSQDKMRKL

FSFVPSWNLT CKDSLLQALK EIHPYLVMDL EQS
Pyrin domain: 1-91
CARD domain: 105-193

ASC Linker peptide
                                              SEQ ID NO: 3
GSGAAPAGIQ APPQS ASC Helix 4 peptide
                                              SEQ ID NO: 4
NPSKMRKLFS FTPAWNWTC

SEQ ID NO: 5
CKDLLLQALR ESQSYLVEDL ERS

Human ACS peptide sequence
                                              SEQ ID NO: 6
MGRARDAIL DALENL Human ACS peptide sequence
                                              SEQ ID NO: 7
ELKKFKLKLL SV Human ACS peptide sequence
                                              SEQ ID NO: 8
REGYGRIPRG ALL Human ACS peptide sequence
                                              SEQ ID NO: 9
DALDLTDKLV SFY Human ACS peptide sequence
                                              SEQ ID NO: 10
DQHRAALIAR Human ACS peptide sequence
                                              SEQ ID NO: 11
TNVEWLLDAL Y Human ACS peptide sequence
                                              SEQ ID NO: 12
DEQYQAVRAE Mouse ACS peptide sequence
                                              SEQ ID NO: 13
ELKKFKMKLL TV Mouse ACS peptide sequence
                                              SEQ ID NO: 14
QLREGYGRIP RGALL Mouse ACS peptide sequence
                                              SEQ ID NO: 15
DAIDLTDKLV SYY Mouse ACS peptide sequence
                                              SEQ ID NO: 16
DQHRQALIAR Mouse ACS peptide sequence
                                              SEQ ID NO: 17
TEVDGVLDAL Mouse ACS peptide sequence
                                              SEQ ID NO: 18
EGQYQAVRAE Mouse ACS peptide sequence
                                              SEQ ID NO: 19
DKMRKLFSFV PSWN Mouse ACS peptide sequence
                                              SEQ ID NO: 20
KEIHPYLVMD LEQS Mouse ACS peptide sequence
                                              SEQ ID NO: 21
AAAASVPAQS TAR linker
                                              SEQ ID NO: 22
GGGC linker
                                              SEQ ID NO: 23
CGGG
```

What is claimed is:

1. An immunogen comprising:
an immunogenic carrier comprising a Qβ bacteriophage virus-like particle (VLP); and
a first antigenic apoptosis-associated speck-like protein containing a caspase activation and recruitment domain (ASC) peptide linked to the immunogenic carrier.

2. The immunogen of claim 1, wherein the first ASC peptide comprises the amino acid sequence of SEQ ID NO: 1 or an antigenic fragment thereof.

3. The immunogen of claim 2, wherein the fragment of SEQ ID NO:1 comprises SEQ ID NO:3, SEQ ID NO:4, or SEQ ID NO:5.

4. The immunogen of claim 1, wherein the immunogenic carrier is linked to the first ASC peptide through a succinimidyl-6-[β-maleimidopropionamido]hexanoate (SMPH) cross-linker molecule.

5. The immunogen of claim 1, further comprising a second antigenic ASC peptide.

6. The immunogen of claim 5, wherein the first antigenic ASC peptide and the second ASC peptide are displayed on a single VLP.

7. A composition comprising the immunogen of claim 1.

8. The composition of claim 7, comprising:
a first population of Qβ VLPs displaying the first antigenic ASC peptide; and
a second population of VLPs displaying a second antigenic ASC peptide.

9. The composition of claim 7, further comprising an adjuvant.

10. A method for treating an inflammatory condition in a subject, the method comprising administering to the subject a therapeutically effective amount of a composition comprising an immunogen, the immunogen comprising:
a first immunogenic carrier comprising a Qβ bacteriophage virus-like particle (VLP); and
a first antigenic apoptosis-associated speck-like protein containing a caspase activation and recruitment domain (ASC) peptide linked to the first immunogenic carrier.

11. The method of claim 10, wherein the method further comprises administering to the subject at least one additional therapeutic agent for treating an inflammatory condition.

12. The method of claim 10, wherein the immunogen further comprises a second antigenic ASC peptide.

13. The method of claim 12, wherein the first antigenic ASC peptide and the second antigenic peptide are displayed on a single Qβ VLP.

14. The method of claim 10, wherein the composition comprises:
a first population of immunogens comprising a first population of Qβ immunogenic carriers each comprising the first antigenic ASC peptide linked to the first Qβ immunogenic carrier; and
a second population of immunogens comprising a second population of immunogenic carriers each comprising a second ASC peptide linked to a second immunogenic carrier.

15. The method of claim 10, wherein at least one antigenic ASC peptide comprises the amino acid sequence of SEQ ID NO: 1 or an antigenic fragment thereof.

16. The method of claim 15, wherein the fragment of SEQ ID NO:1 comprises SEQ ID NO:3, SEQ ID NO:4, or SEQ ID NO:5.

17. The method of claim 10, wherein the composition is administered to the subject before the subject manifests a symptom or clinical sign of the inflammatory condition.

18. A vaccine comprising the immunogen of claim 1.

19. A method for vaccinating a subject against an inflammatory condition, the method comprising administering to the subject a therapeutically effective amount of the vaccine of claim 18.

20. The method of claim 19, wherein the method further comprises administering to the subject at least one additional therapeutic agent for treating the inflammatory condition.

21. The method of claim 19, wherein the vaccine is administered before the subject manifests a symptom or clinical sign of the inflammatory condition.

22. The method of claim 21, wherein the method further comprises administering to the subject at least one additional therapeutic agent for treating the inflammatory condition.

* * * * *